(12) United States Patent
Turchetta et al.

(10) Patent No.: US 9,206,229 B2
(45) Date of Patent: Dec. 8, 2015

(54) BORTEZOMIB ESTERS AND FORMULATIONS THEREOF

(71) Applicant: CHEMI S.P.A., Cinisello Balsamo (IT)

(72) Inventors: Stefano Turchetta, Patrica (IT); Maurizio Zenoni, Patrica (IT); Umberto Ciambecchini, Patrica (IT); Paolo Brandi, Patrica (IT); Vincenzo De Sio, Patrica (IT); Giorgio Berardi, Patrica (IT)

(73) Assignee: CHEMI S.P.A., Cinisello Balsamo (IT)

( * ) Notice: Subject to any disclaimer, the term of this patent is extended or adjusted under 35 U.S.C. 154(b) by 0 days.

(21) Appl. No.: 14/419,493

(22) PCT Filed: Aug. 1, 2013

(86) PCT No.: PCT/EP2013/066224
§ 371 (c)(1),
(2) Date: Feb. 4, 2015

(87) PCT Pub. No.: WO2014/023647
PCT Pub. Date: Feb. 13, 2014

(65) Prior Publication Data
US 2015/0232508 A1    Aug. 20, 2015

(30) Foreign Application Priority Data
Aug. 6, 2012 (IT) .............................. MI2012A1394

(51) Int. Cl.
*A61K 38/00* (2006.01)
*C07K 5/06* (2006.01)
*C07K 5/065* (2006.01)

(52) U.S. Cl.
CPC .................................. *C07K 5/06078* (2013.01)

(58) Field of Classification Search
CPC ..... A61K 38/00; A61K 31/58; A61K 31/506; A61K 31/69; A61K 38/05
See application file for complete search history.

(56) References Cited

FOREIGN PATENT DOCUMENTS

WO    2009154737    12/2009

OTHER PUBLICATIONS

International Search Report of PCT/EP2013/066224 mailed Oct. 23, 2013.
Written Opinion of PCT/EP2013/066224 mailed Oct. 23, 2013.

*Primary Examiner* — Marcela M Cordero Garcia
*Assistant Examiner* — Kaipeen Yang
(74) *Attorney, Agent, or Firm* — Silvia Salvadori, P.C.; Silvia Salvadori

(57) ABSTRACT

Bortezomib esters with tartaric acid wherein the molar ratio between bortezomib and tartaric acid is 2:1 and formulations containing them are described.

7 Claims, 22 Drawing Sheets

FIGURE 15B

| Pos. [°2Th.] | Height [cts] | FWHM [°2Th.] | d-spacing [Å] | Rel. Int. [%] |
|---|---|---|---|---|
| 3,2785 | 349,40 | 0,1171 | 26,94992 | 17,98 |
| 5,9922 | 1114,05 | 0,1171 | 14,74979 | 57,32 |
| 6,4119 | 1076,13 | 0,1171 | 13,78509 | 55,37 |
| 6,9310 | 958,05 | 0,0502 | 12,75376 | 49,29 |
| 7,7752 | 1852,45 | 0,1338 | 11,37082 | 95,31 |
| 7,9776 | 1943,62 | 0,1506 | 11,08278 | 100,00 |
| 8,3486 | 1927,07 | 0,1338 | 10,59112 | 99,15 |
| 9,4337 | 632,38 | 0,1338 | 9,37523 | 32,54 |
| 11,2230 | 778,59 | 0,1840 | 7,88416 | 40,06 |
| 11,7987 | 388,37 | 0,1338 | 7,50075 | 19,98 |
| 12,2044 | 757,98 | 0,2342 | 7,25230 | 39,00 |
| 12,9037 | 187,56 | 0,1004 | 6,86082 | 9,65 |
| 13,2863 | 237,09 | 0,1338 | 6,66411 | 12,20 |
| 14,9816 | 179,94 | 0,3346 | 5,91358 | 9,26 |
| 15,9587 | 403,71 | 0,1673 | 5,55366 | 20,77 |
| 17,0235 | 197,21 | 0,1338 | 5,20861 | 10,15 |
| 18,5339 | 312,95 | 0,2342 | 4,78740 | 16,10 |
| 19,3046 | 894,74 | 0,2676 | 4,59798 | 46,03 |
| 20,1111 | 766,69 | 0,2342 | 4,41538 | 39,45 |
| 20,5087 | 1121,01 | 0,2007 | 4,33066 | 57,68 |
| 21,7532 | 281,21 | 0,2007 | 4,08564 | 14,47 |
| 22,3896 | 205,95 | 0,3346 | 3,97092 | 10,60 |
| 23,5220 | 193,62 | 0,2676 | 3,78227 | 9,96 |
| 24,3860 | 195,34 | 0,2676 | 3,65017 | 10,05 |
| 25,0875 | 104,71 | 0,2676 | 3,54968 | 5,39 |
| 26,0747 | 125,41 | 0,2342 | 3,41749 | 6,45 |
| 27,4549 | 45,45 | 0,4684 | 3,24874 | 2,34 |
| 28,5096 | 74,26 | 0,3346 | 3,13091 | 3,82 |
| 29,5356 | 125,70 | 0,1004 | 3,02444 | 6,47 |
| 31,6032 | 44,84 | 0,9368 | 2,83113 | 2,31 |
| 33,1621 | 39,02 | 0,4015 | 2,70152 | 2,01 |

FIGURE 16B

| Pos. [°2Th.] | Height [cts] | FWHM [°2Th.] | d-spacing [Å] | Rel. Int. [%] |
|---|---|---|---|---|
| 5,6952 | 144,58 | 0,1673 | 15,51827 | 8,09 |
| 6,2255 | 343,42 | 0,0836 | 14,19755 | 19,23 |
| 7,8274 | 1786,13 | 0,1004 | 11,29508 | 100,00 |
| 8,2003 | 606,89 | 0,1338 | 10,78237 | 33,98 |
| 9,4174 | 73,30 | 0,1338 | 9,39142 | 4,10 |
| 10,6073 | 68,33 | 0,1004 | 8,34039 | 3,83 |
| 11,1369 | 143,95 | 0,0669 | 7,94494 | 8,06 |
| 11,5878 | 114,01 | 0,1004 | 7,63676 | 6,38 |
| 12,0322 | 344,62 | 0,0669 | 7,35572 | 19,29 |
| 13,4461 | 196,01 | 0,2007 | 6,58525 | 10,97 |
| 14,6547 | 123,30 | 0,2007 | 6,04477 | 6,90 |
| 15,7877 | 275,74 | 0,1338 | 5,61341 | 15,44 |
| 16,8887 | 204,30 | 0,1673 | 5,24988 | 11,44 |
| 18,4462 | 118,07 | 0,1004 | 4,80995 | 6,61 |
| 19,2930 | 177,67 | 0,3011 | 4,60071 | 9,95 |
| 19,8016 | 281,75 | 0,1004 | 4,48367 | 15,77 |
| 20,4215 | 235,24 | 0,1004 | 4,34896 | 13,17 |
| 21,4358 | 296,62 | 0,0669 | 4,14540 | 16,61 |
| 21,9267 | 43,32 | 0,1004 | 4,05369 | 2,43 |
| 22,6669 | 129,97 | 0,1338 | 3,92297 | 7,28 |
| 23,4327 | 91,32 | 0,1673 | 3,79647 | 5,11 |
| 24,3559 | 85,11 | 0,4015 | 3,65462 | 4,76 |
| 25,1677 | 49,58 | 0,2007 | 3,53855 | 2,78 |
| 27,9407 | 30,14 | 0,2007 | 3,19334 | 1,69 |
| 28,4047 | 24,25 | 0,2007 | 3,14223 | 1,36 |
| 29,5175 | 28,81 | 0,2676 | 3,02625 | 1,61 |
| 31,5464 | 25,32 | 0,2007 | 2,83610 | 1,42 |
| 32,9094 | 14,63 | 0,5353 | 2,72169 | 0,82 |

FIGURE 18B

| Pos. [°2Th.] | Height [cts] | FWHM [°2Th.] | d-spacing [Å] | Rel. Int. [%] |
|---|---|---|---|---|
| 6,2608 | 456,34 | 0,1171 | 14,11759 | 23,73 |
| 6,6025 | 188,05 | 0,1338 | 13,38766 | 9,78 |
| 7,8135 | 1653,86 | 0,1338 | 11,31516 | 86,01 |
| 8,1682 | 1922,95 | 0,1004 | 10,82468 | 100,00 |
| 9,4419 | 100,65 | 0,2007 | 9,36708 | 5,23 |
| 10,5511 | 227,28 | 0,1673 | 8,38472 | 11,82 |
| 11,1221 | 256,71 | 0,1673 | 7,95550 | 13,35 |
| 11,5601 | 211,22 | 0,1338 | 7,65501 | 10,98 |
| 12,0805 | 781,79 | 0,1004 | 7,32644 | 40,66 |
| 13,1804 | 489,32 | 0,1673 | 6,71741 | 25,45 |
| 14,6769 | 249,52 | 0,1338 | 6,03566 | 12,98 |
| 15,8181 | 355,09 | 0,2007 | 5,60270 | 18,47 |
| 16,9310 | 311,94 | 0,1004 | 5,23684 | 16,22 |
| 17,5407 | 86,45 | 0,1004 | 5,05618 | 4,50 |
| 17,8636 | 56,12 | 0,1338 | 4,96551 | 2,92 |
| 18,4296 | 226,72 | 0,1004 | 4,81425 | 11,79 |
| 19,1077 | 252,86 | 0,1004 | 4,64491 | 13,15 |
| 19,4926 | 344,63 | 0,1004 | 4,55406 | 17,92 |
| 19,7697 | 552,45 | 0,0836 | 4,49084 | 28,73 |
| 20,3984 | 692,96 | 0,1171 | 4,35384 | 36,04 |
| 20,7196 | 409,67 | 0,1338 | 4,28705 | 21,30 |
| 21,4746 | 259,40 | 0,1673 | 4,13800 | 13,49 |
| 22,7650 | 147,62 | 0,1338 | 3,90630 | 7,68 |
| 23,3709 | 199,58 | 0,2007 | 3,80636 | 10,38 |
| 23,9769 | 72,98 | 0,5353 | 3,71153 | 3,80 |
| 24,3873 | 177,76 | 0,1673 | 3,64999 | 9,24 |
| 25,0115 | 119,58 | 0,1338 | 3,56029 | 6,22 |
| 25,5318 | 95,14 | 0,1338 | 3,48890 | 4,95 |
| 26,1858 | 60,54 | 0,2676 | 3,40324 | 3,15 |
| 26,9623 | 84,46 | 0,2007 | 3,30696 | 4,39 |
| 27,4363 | 33,59 | 0,2007 | 3,25089 | 1,75 |
| 27,9996 | 41,67 | 0,2342 | 3,18676 | 2,17 |
| 29,5120 | 42,12 | 0,3346 | 3,02681 | 2,19 |
| 31,4367 | 66,24 | 0,2007 | 2,84574 | 3,44 |
| 32,8021 | 57,10 | 0,1338 | 2,73035 | 2,97 |
| 34,3016 | 18,69 | 0,5353 | 2,61434 | 0,97 |
| 37,0577 | 26,58 | 0,4015 | 2,42599 | 1,38 |
| 39,2766 | 19,46 | 0,4015 | 2,29390 | 1,01 |

BORTEZOMIB ESTERS AND FORMULATIONS THEREOF

This application is a U.S. National Stage of PCT/EP2013/066224 filed 1 Aug. 2013, which claims priority to and the benefit of Italian Application No. MI2012A001394 filed 6 Aug. 2012, the contents of which applications are incorporated herein by reference in their entirety.

The present invention relates to bortezomib esters, more particularly to bortezomib esters with tartaric acid, and to stable formulations containing them.

The active ingredient bortezomib, the chemical compound of formula I

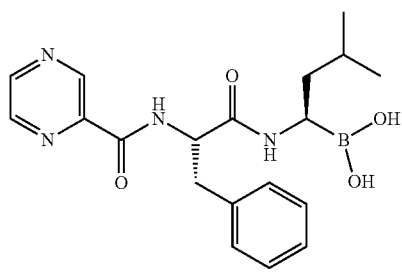

(I)

is a dipeptide wherein one of the two amino acids is an aminoboronic acid. Bortezomib belongs to the therapeutic class of proteasome inhibitors, a cellular protein complex having the function of degrading the proteins to be eliminated. The inhibitory effect of bortezomib on proteasome interferes with the intracellular processes for protein turnover, with the consequent beginning of a degenerative state of the cell leading to its death. For this pharmacological action bortezomib has been approved for the treatment of forms of multiple myeloma which were already treated with at least another therapeutic agent.

The active ingredient is on the market under the tradename Velcade® as lyophilized powder containing mannitol esters of bortezomib which is administered by intravenous route after reconstitution of the lyophilizate with physiologic solution where the active ingredient is reconstituted by hydrolysis.

Bortezomib was first described in U.S. Pat. No. 5,780,454 with the code MG-341. The compound is isolated as trimeric boroxine of formula (II)

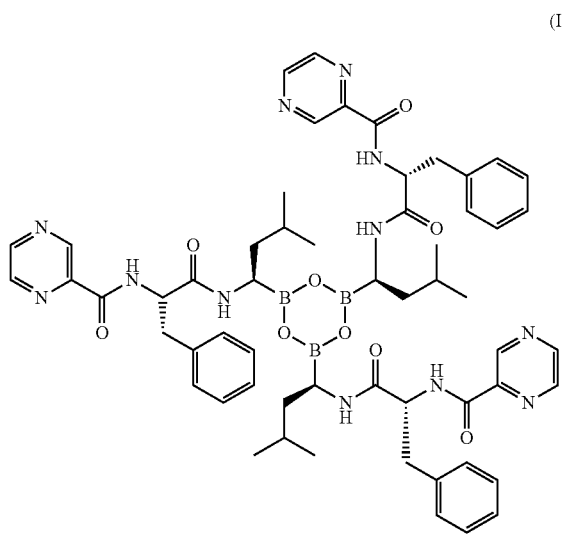

(II)

Bortezomib Boroxine
(Trimeric form)

as described in U.S. Pat. No. 6,699,835.

The formulation of bortezomib as lyophylized powder consisting of its mannitol esters was developed to overcome the difficulties due to the poor water solubility of the active ingredient as such and to its instability.

In fact, in example 5 of U.S. Pat. No. 6,958,319 it was reported that the active ingredient as white amorphous powder is stable for more than 2 years (HPLC purity>97%) when stored at −20° C., but it is not stable for more than 3-6 months when stored at 2-8° C.; the liquid formulation consisting of the active ingredient in 0.5 mg/ml concentration in aqueous NaCl 0.9% solution containing also 2% v/v ethanol and 0.1% ascorbic acid is not stable for more than 6 months when stored at 2-8° C.

On the contrary, the formulation of bortezomib as lyophilized mannitol esters allows to obtain a powder which is stable also after 18 months when stored at 5° C., 37° C. or 50° C.: said powder, after reconstitution with a NaCl 0.9% solution to be administered intravenously, dissolves within 10 seconds resulting in a clear colorless solution containing the active ingredient as boronic acid obtained by complete hydrolysis of the ester.

Further formulations of bortezomib have been described in the literature, in addition to those containing its esters with mannitol or sugars in general, disclosed in U.S. Pat. No. 6,958,319 and related patents U.S. Pat. No. 6,713,446 and U.S. Pat. No. 6,958,319.

WO2009154737 discloses esters of bortezomib with α-hydroxycarboxylic acids, in particular citric acid, and their formulations.

WO2010039762 discloses liquid formulations of bortezomib in an organic solvent.

WO2010089768 discloses a bortezomib formulation wherein the active ingredient is lyophilized with tromethamol.

WO2010114982 discloses lyophilized containing bortezomib, cyclodextrin and at least a filler or a surfactant.

US20110230441 discloses a liquid formulation of bortezomib wherein the solvent is mainly propylen glycol.

Formulating bortezomib is still a problem difficult to solve and there is the need of bortezomib formulations having improved stability and solubility characteristics.

We have now found bortezomib esters, in particular bortezomib esters with tartaric acid wherein bortezomib and tartaric acid are in 2:1 molar ratio which allow to obtain particularly stable and soluble formulations.

Therefore, object of the present invention are bortezomib esters with tartaric acid wherein bortezomib and tartaric acid are in molar ratio 2:1, and in particular the bortezomib esters of formula (III) and formula (IV)

As used herein, unless otherwise specified, tartaric acid means L-tartaric acid, D-tartaric acid or meso-tartaric acid.

As used herein, the bortezomib-tartrate 2:1 esters (also called bis-bortezomib tartrate) object of the present invention will be also indicated as:

(5+5) bortezomib-tartrate 2:1 or (5+5) bis-bortezomib tartrate for the compounds of formula III and, (6+6) bortezomib-tartrate 2:1 or (6+6) bis-bortezomib tartrate for the compounds of formula IV.

The esters object of the present invention, formulated in combination with pharmaceutically acceptable excipients, result in stable formulations which can be reconstituted with physiologic solution to obtain injectable clear solutions containing bortezomib as active ingredient.

Therefore, a further object of the present invention are formulations of esters of bortezomib with tartaric acid wherein bortezomib and tartaric acid are in a molar ratio 2:1, in particular of esters of formula III and IV, in admixture with pharmaceutically acceptable excipients and the injectable solutions obtained by reconstituting said formulations with physiologically compatible solutions.

The esters of bortezomib with tartaric acid object of the present invention are prepared by reacting bortezomib, preferably bortezomib boroxine, with tartaric acid or a salt thereof.

In particular, the bortezomib esters of formula III object of the present invention are prepared by reacting tartaric acid, preferably L-tartaric acid, and bortezomib, preferably bortezomib boroxine, in a suitable solvent according to the following scheme wherein the reaction with L-tartaric acid is depicted:

-continued

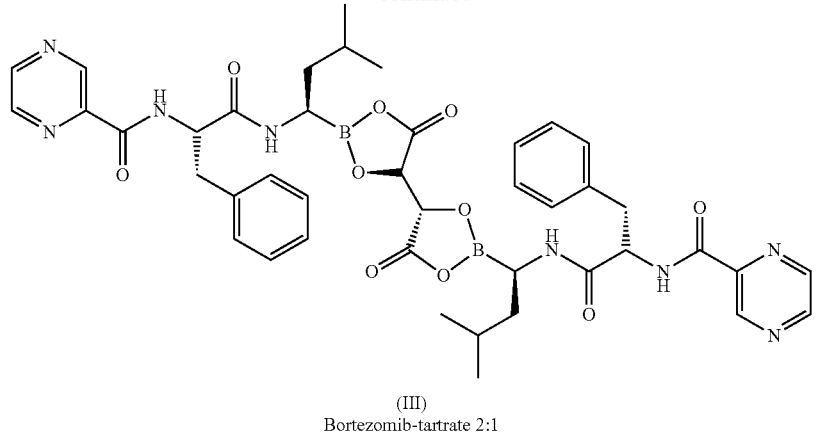

(III)
Bortezomib-tartrate 2:1

As already reported, bortezomib is isolated as trimeric form (boroxine) and therefore the esters of formula III object of the present invention are prepared by reacting two moles of boroxine with three moles of tartaric acid.

In a preferred practical embodiment of the present invention, (5+5) bis-bortezomib tartrate III is prepared by reacting boroxine and L-tartaric acid. Boroxine is dissolved in a suitable organic solvent and L-tartaric acid, optionally dissolved in a suitable organic acid, is added to the resultant solution. The resultant solution is concentrated under vacuum up to a solid residue or added with a suitable co-solvent obtaining the solid by precipitation. The resultant solid product is isolated and dried under vacuum obtaining (5+5) bis-bortezomib tartrate III with high purity.

Examples of suitable solvents are alcohols, such as $C_{1-3}$ alcohols, for example methanol, ethanol and isopropanol, ketones, for example acetone and methylethylketone, alkyl halides, for example dichloromethane and chloroform, esters, for example ethyl acetate and isopropyl acetate, or nitriles, for example acetonitrile and propionitrile.

The molar ratio between boroxine and the used tartaric acid is 0.67±0.05 corresponding to a molar ratio between boronic acid and tartaric acid from 1.9 to 2.2. (5+5) bis-bortezomib tartrate III is isolated in a particularly pure form, generally with purity>99.5%.

The bortezomib esters of formula IV object of the present invention are prepared by reacting tartaric acid salts, preferably sodium salts, and bortezomib, preferably bortezomib boroxine, in a suitable solvent according to the following scheme wherein the reaction with L-tartaric acid sodium salt is depicted:

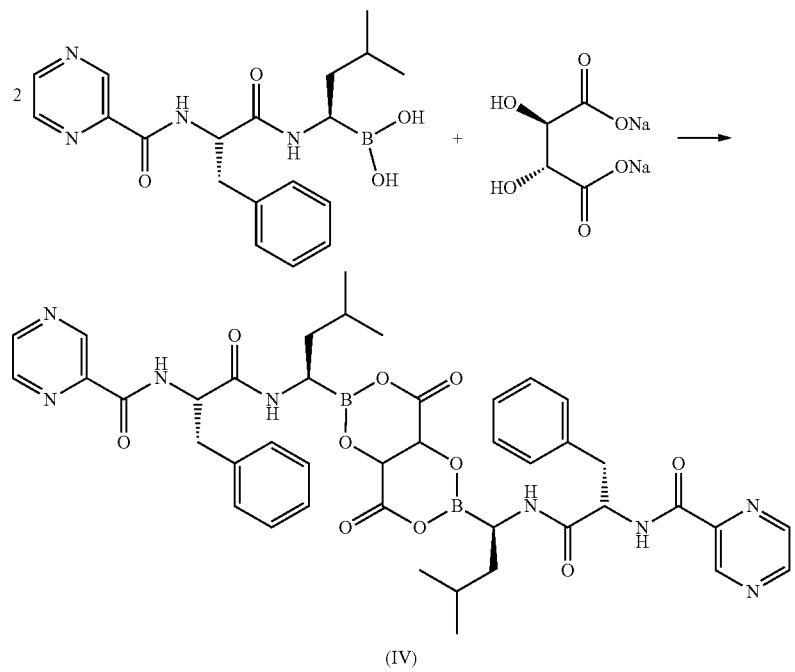

(IV)

As already reported, bortezomib is isolated as trimeric form (boroxine) and therefore the esters of formula IV object of the present invention are prepared by reacting two moles boroxine with three moles tartaric acid sodium salt.

In a preferred practical embodiment of the present invention, (6+6) bis-bortezomib tartrate IV is prepared by reacting boroxine and L-tartaric acid sodium salt. Boroxine is dissolved in a suitable organic solvent and L-tartaric acid sodium salt, optionally dissolved in a suitable organic acid, is added to the resultant solution. The resultant solution is concentrated under vacuum up to a solid residue or added with a suitable co-solvent obtaining the solid by precipitation. The resultant solid product is isolated and dried under vacuum obtaining (6+6) bis-bortezomib tartrate IV with high purity.

Examples of suitable solvents are alcohols, such as $C_{1-3}$ alcohols, for example methanol, ethanol and isopropanol, ketones, for example acetone and methylethylketone, alkyl halides, for example dichloromethane and chloroform, esters, for example ethyl acetate and isopropyl acetate, or nitriles, for example acetonitrile and propionitrile.

The molar ratio between boroxine and the used tartaric acid salt is 0.67±0.05 corresponding to a molar ratio between boronic acid and tartaric acid from 1.9 to 2.2.

(6+6) bis-bortezomib tartrate IV is isolated in a particularly pure form, generally with purity>99.5%.

The compound of formula IV shows different polymorphic forms and an amorphous form.

Two polymorphic forms, named A and B, and an amorphous form of (6+6) bis-bortezomib tartrate of formula IV have been characterized by X-ray diffraction (PXRD) under the following experimental conditions:
Type of instrument: X'Pert PRO PANalytical
Type of measurement: Single scan
Wave lengths of measurement: Cu Kα1
Material constituting the anode: Cu
Voltage of the X-ray tube: 40
Power of the X-ray tube (mA): 40
Type of movement of the sample: Rotation
Rotation time of the sample (s): 1.0
Thickness of the filter (mm): 0.020
Filter material: Ni
Detector's name: X'Celerator
Type of detector: RTMS detector
Scan axis: Gonio
Scan range)(°): 3.0000-39.9987
Width of the measurement range)(°): 0.0167
Number of points: 2214
Scan mode: Continuous
Counting time (s): 12.700
Application software: X'Pert Data Collector vs. 2.2d
Control software of the instrument: XPERT-PRO vs. 1.9B
Temperature Room temperature Form A of (6+6) bis-bortezomib tartrate of formula IV is an object of the present invention.

Form A is obtained as described in example 5 and shows a PXRD with peaks at 9.94, 14.37, 15.66, 19.02, 19.80, 24.65, 25.57, 26.82, 30.32, 31.37, 32.12, 33.75, 34.30, 36.29 and 38.98±0.20 2theta.

Form B of (6+6) bis-bortezomib tartrate of formula IV is an object of the present invention.

Form B is obtained as described in example 6 and shows a PXRD with peaks at 3.39, 5.77, 6.69, 8.09, 8.78, 9.31, 10.03, 18.71, 19.12, 23.29 and 23.59±0.20 2theta.

Amorphous form of (6+6) bis-bortezomib tartrate of formula IV is an object of the present invention.

The amorphous form is obtained as described in example 7.

The production of (5+5) bis-bortezomib tartrate of formula III and of (6+6) bis-bortezomib tartrate of formula IV in particularly pure form by reacting bortezomib with tartaric acid and bortezomib with a tartaric acid salt according to the present invention is an unexpected result with respect to what described in the prior art. In fact, in the already cited patent application WO2009154737 the preparation of a covalent 1:1 compound between bortezomib and tartaric acid according to the following scheme is described:

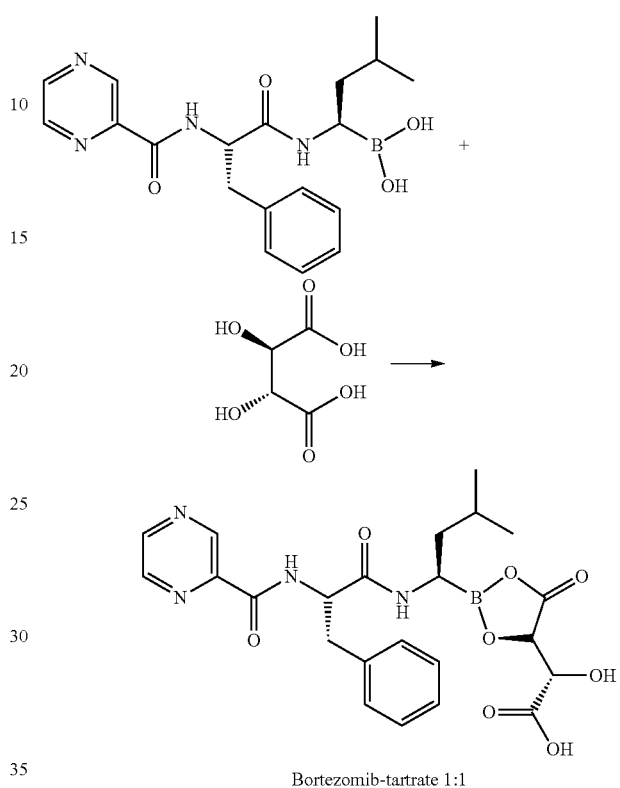

Bortezomib-tartrate 1:1

In particular, in example 26 of WO2009154737, (R)-2-hydroxy-2-((R)-2-((R)-3-methyl-1((S)-3-phenyl-2-(pyrazin-2-carboxyamido)-propanamido)butyl)-5-oxo-1,3,2-dioxaborolan-4-yl)acetic acid is obtained by reacting 0.737 mmoles bortezomib with 1 mmole L-tartaric acid in acetone while, in example 27, (S)-2-hydroxy-2-((S)-2-((R)-3-methyl-1((S)-3-phenyl-2-(pyrazin-2-carboxyamido)propanamido)butyl)-5-oxo-1,3,2-dioxaborolan-4-yl)acetic acid is obtained by reacting 0.491 mmoles bortezomib with 0.983 mmole D-tartaric acid.

In both examples the compound bortezomib tartrate 1:1 is obtained as main product in admixture with a dimeric species for which no characterization is given.

The compounds of formula III and IV object of the present invention are obtained with high purity by reacting boroxine with tartaric acid and by reacting boroxine with a tartaric acid salt respectively, and their structure has been characterized as (5+5) bis-bortezomib tartrate of formula III and (6+6) bis-bortezomib tartrate of formula IV. The compounds object of the present invention, when formulated in combination with pharmaceutically acceptable excipients, result in stable formulations.

Said formulations can be solid, for example physical mixtures of powders or lyophilized powders, or liquid, for example concentrated solutions in a suitable organic solvent optionally added with suitable excipients and/or stabilizing agents. Suitable solid formulations are those obtained by making a solid mixture of a compound object of the present invention with mannitol or inorganic salts or by lyophilizing a mixture of a compound according to the present invention with mannitol or inorganic salts.

Suitable liquid formulations are concentrated solutions of a compound according to the present invention in dimethylsulfoxide optionally added with suitable excipients and/or stabilizing agents.

The stability of the compounds object of the present invention and of the formulation containing them has been evaluated through stability tests under ICH storage (25° C., 60% relative humidity) and accelerated (40° C., 75% relative humidity) conditions by collecting the HPLC purity data of the tested formulations after two and four weeks. Under all the evaluation conditions, the stability resulted at least comparable with the known formulations, in particular with the formulations described in U.S. Pat. No. 6,958,319.

The formulations object of the present invention are also characterized by a very good solubility in water or aqueous solutions. Once reconstituted with physiologically compatible aqueous solutions, they give rise in short time, generally within one or two minutes, to clear aqueous solutions wherein bis-bortezomib tartrate is completely hydrolyzed to give the corresponding boronic acid and tartaric acid. Also the concentrated liquid formulations of bis-bortezomib tartrate in a suitable pharmaceutically acceptable organic solvent (for example dimethylsulfoxide) are particularly suitable to obtain sterile injectable formulations wherein the active ingredient bortezomib is reconstituted as free boronic acid in solution by adding a suitable amount of a physiologically compatible aqueous solution.

The characteristics of stability and solubility of the formulations object of the present invention make them particularly suitable and advantageous for the use in therapy.

In order to better illustrate the present invention without limiting it, the following examples are now given.

Figure 1:
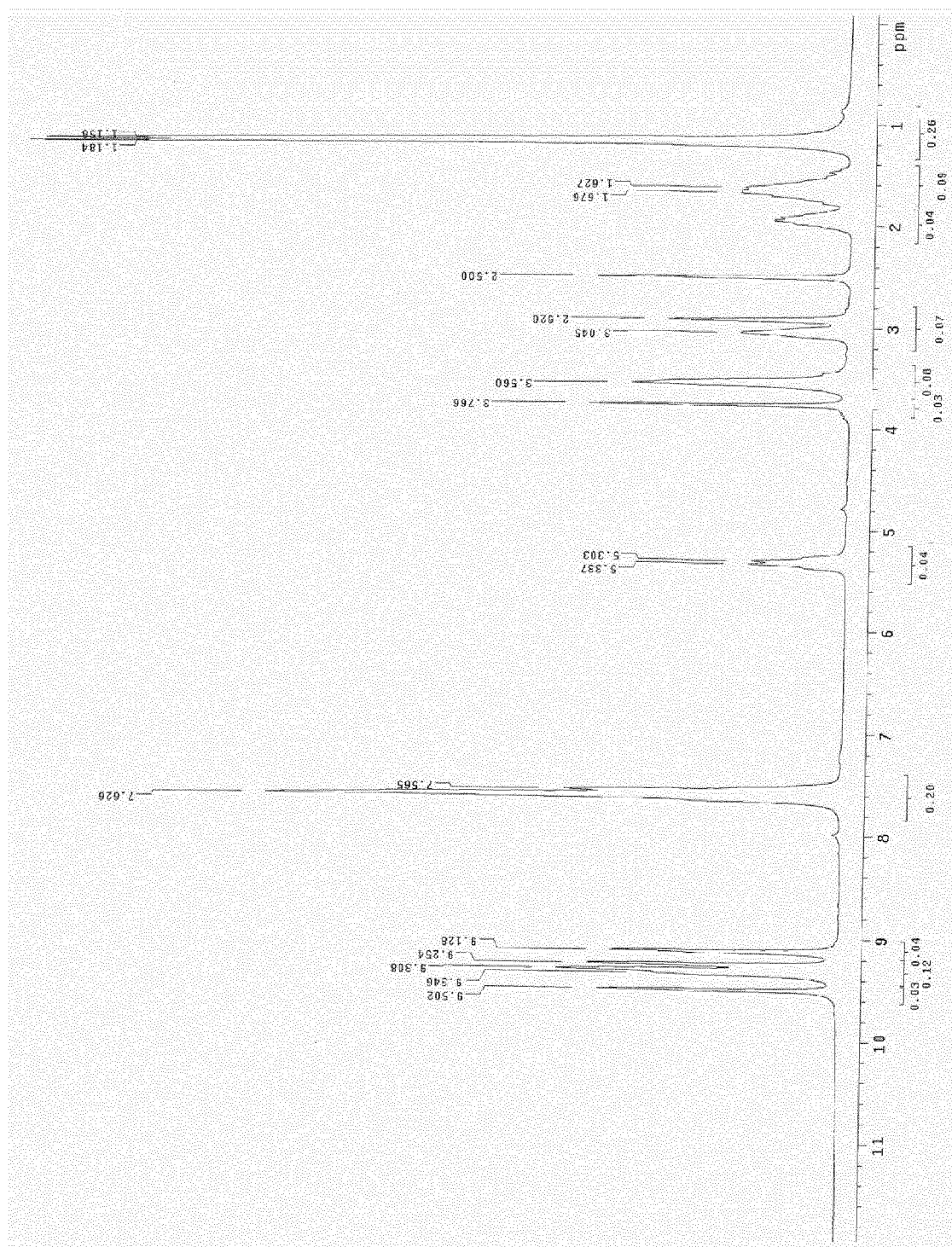
FIG. 1—$^1$H-NMR of Bortezomib boroxine
FIG. 2—$^{13}$C-NMR of Bortezomib boroxine
FIG. 3—IR of Bortezomib boroxine
FIG. 4—$^1$H-NMR of (6+6) bis bortezomib tartrate IV of example 1
FIG. 5—$^{13}$C-NMR of (6+6) bis bortezomib tartrate IV of example 1
FIG. 6—IR of (6+6) bis bortezomib tartrate IV of example 1
FIG. 7—$^1$H-NMR of (5+5) bis bortezomib tartrate III of example 2
FIG. 8—$^{13}$C-NMR of (5+5) bis bortezomib tartrate III of example 2
FIG. 9—IR of (5+5) bis bortezomib tartrate III of example 2
FIG. 10—PXRD of (5+5) bis bortezomib tartrate III of example 2
FIG. 11—PXRD of (6+6) bis bortezomib tartrate IV of example 5
FIG. 12—PXRD of (6+6) bis bortezomib tartrate IV of example 6
FIG. 13—PXRD of (6+6) bis bortezomib tartrate IV of example 7
FIG. 14—DSC of (5+5) bis bortezomib tartrate III of example 2
FIG. 15A—PXRD of (5+5) bis bortezomib tartrate III of example 11
FIG. 15B—peak list of the PXRD of (5+5) bis bortezomib tartrate III of example 11
FIG. 16A—PXRD of (5+5) bis bortezomib tartrate III form A of example 15
FIG. 16B—peak list of the PXRD of (5+5) bis bortezomib tartrate III form A of example 15
FIG. 17—DSC of (5+5) bis bortezomib tartrate III form A of example 15
FIG. 18A—PXRD of (5+5) bis bortezomib tartrate III form A of example 16
FIG. 18B—peak list of the PXRD of (5+5) bis bortezomib tartrate III form A of example 16
FIG. 19—DSC of (5+5) bis bortezomib tartrate III form A of example 16
Figure 2:
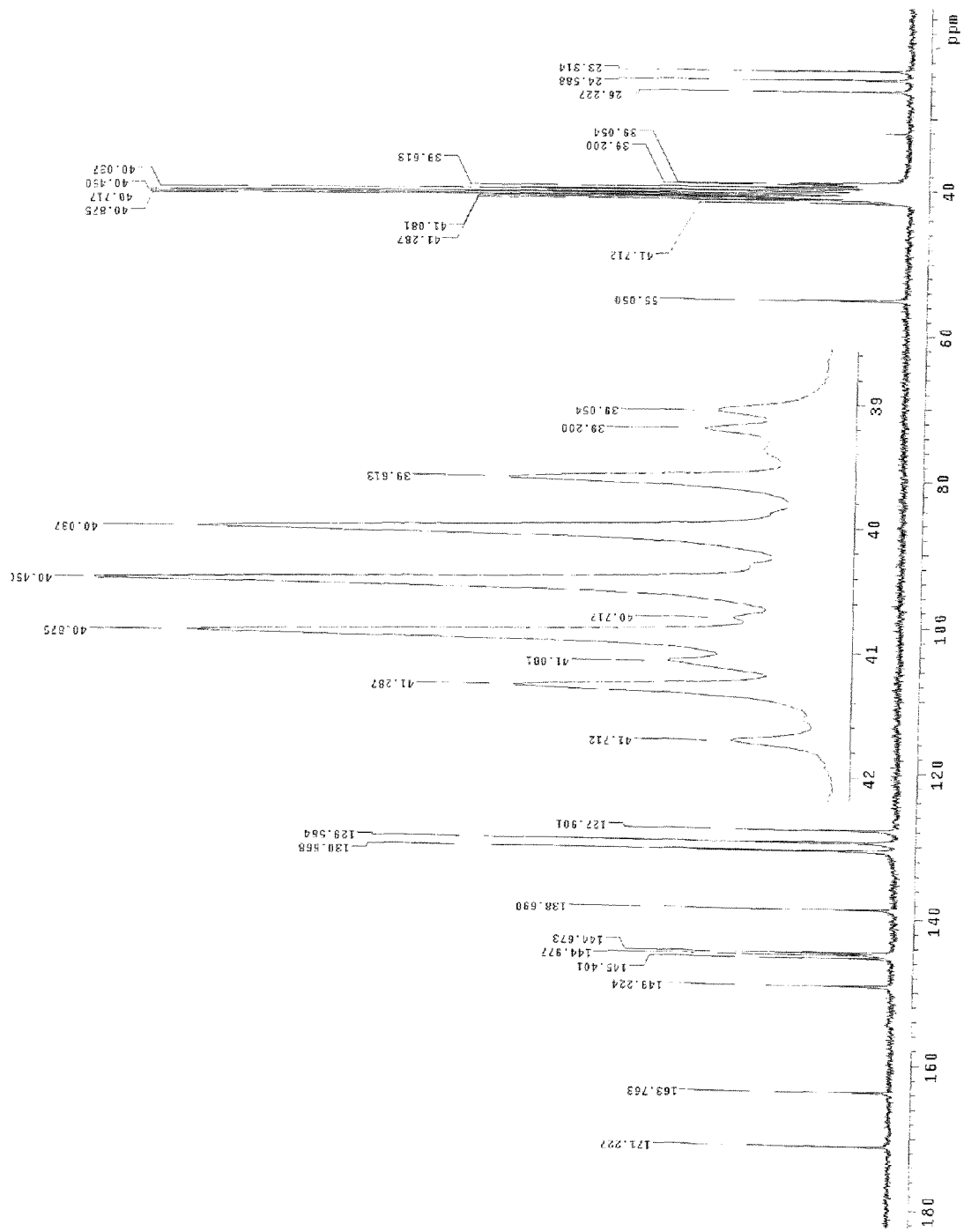
Figure 3:
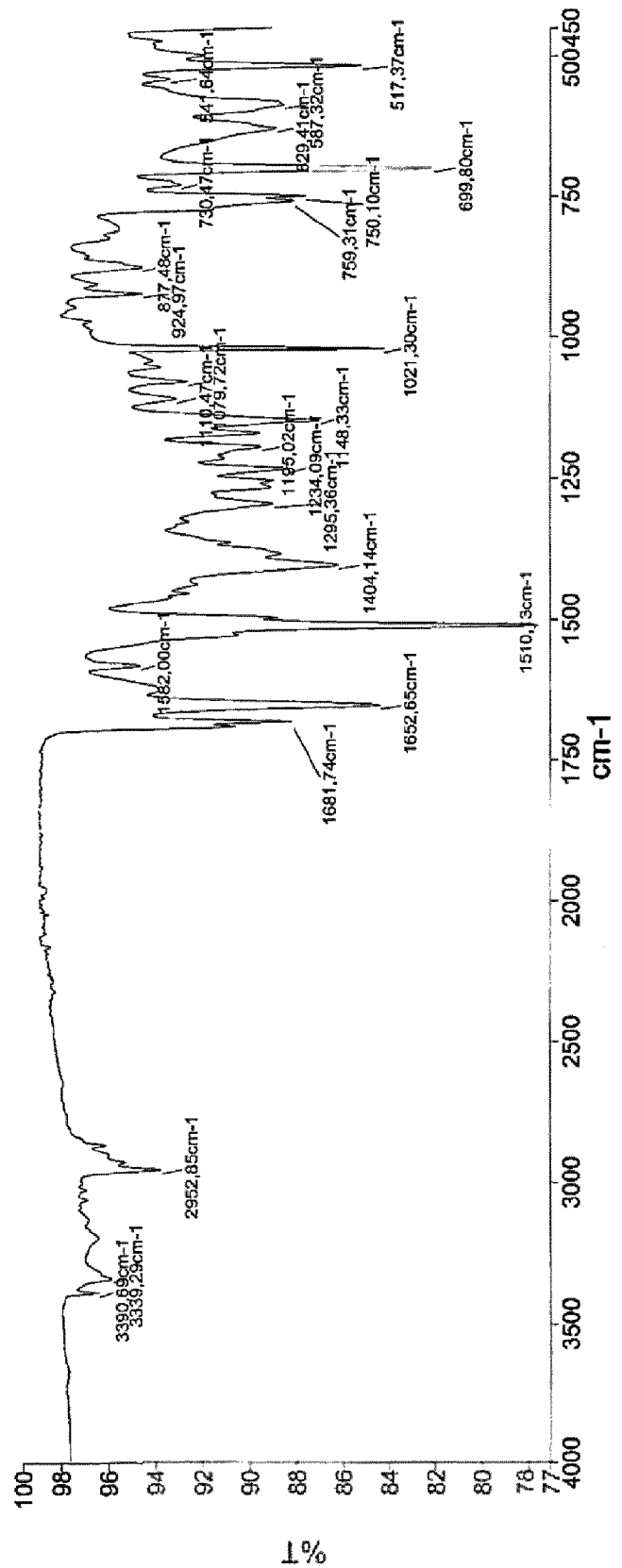

Boroxine used in the experiments described herein after was prepared according to the procedures described in WO2005097809. The characterization of boroxine by $^1$H-NMR, $^{13}$C-NMR and IR spectra is reported in FIGS. 1, 2 and 3.

For the acquisition of the NMR spectra a Varian Gemini VXR 200S 200 MHz spectrometer was used by using DMSO-d$^6$ as solvent, while for the IR spectra a FT-IR ATR (Attenuated Total Reflectance) Perkin Elmer Spectrum Two was used under the following conditions:

Source: MIR
Detector: LiTaO3
Crystal: diamond
Beansplitter: OpTKBr
Window: KBr
Scan range: (4500-400) cm$^{-1}$
Resolution: 4 cm$^{-1}$
Scan speed: 0.2 cm/s
Number scan: 4
Background: AIR The DSC were carried out under the following conditions:
Type of instrument: STA 409 OC Luxx® Netzsch
Heating and cooling speed: 0.01 K/min . . . 50 K/min
TG resolution: up to 0.00002%
DSC resolution: <1 µW (K sensor)
DSC sensitivity: 8 µV/mW (K sensor)
Atmosphere: inert (nitrogen)
Gas flow control: 2 cleaning gasses and 1 protecting gas
Cleaning gas: nitrogen
Cleaning gas speed: 60 ml/min
Protecting gas: nitrogen
Protecting gas speed: 20 ml/min
Melting pan: DSC/TG pan Al
Heating rate: 10° C./min
DSC heating ramp: from 25° C. to 400° C.

EXAMPLE 1

Preparation of (6+6) bis-bortezomib L-tartrate IV from sodium L-tartrate

Figure 4:
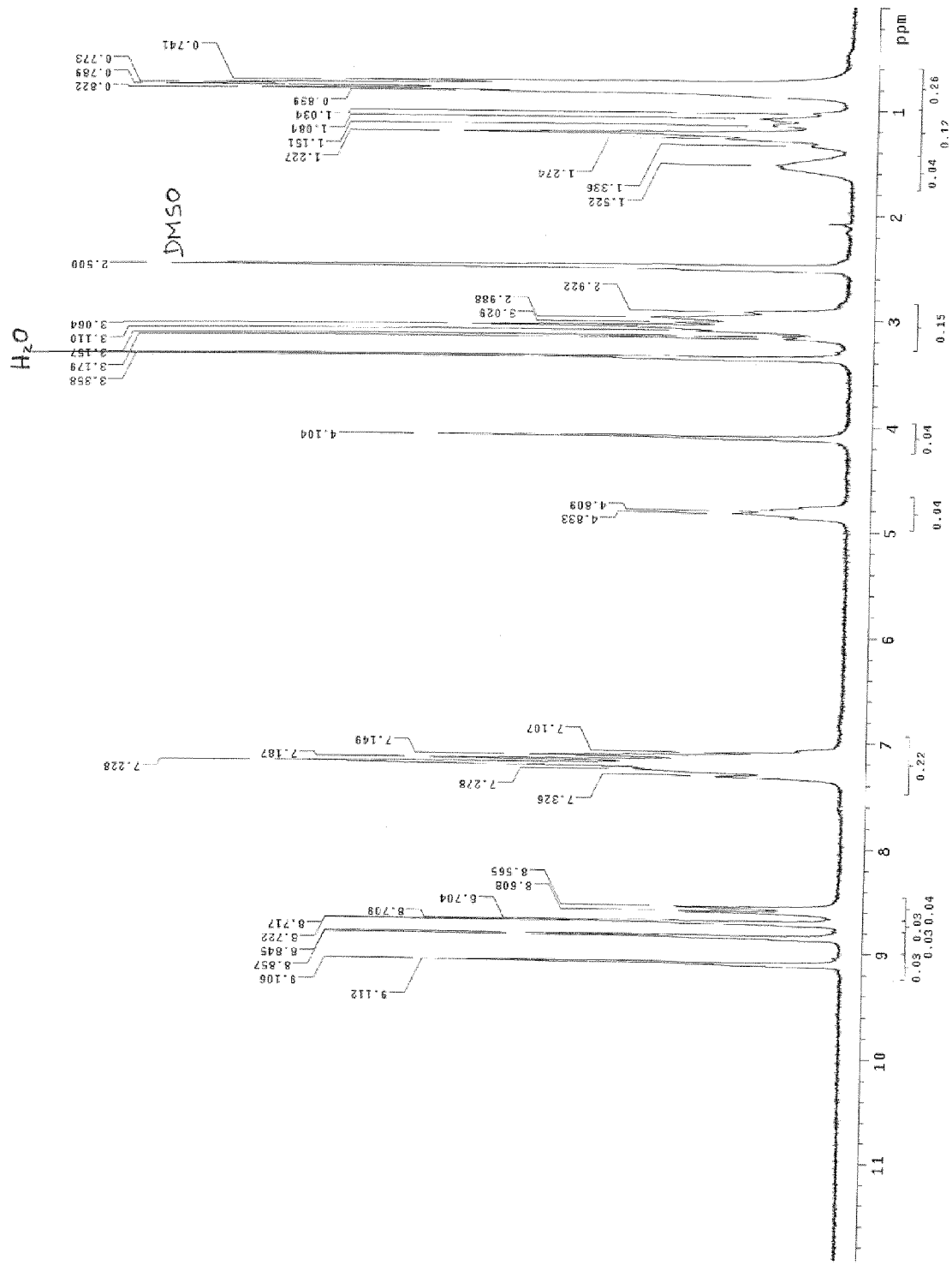
Figure 5:
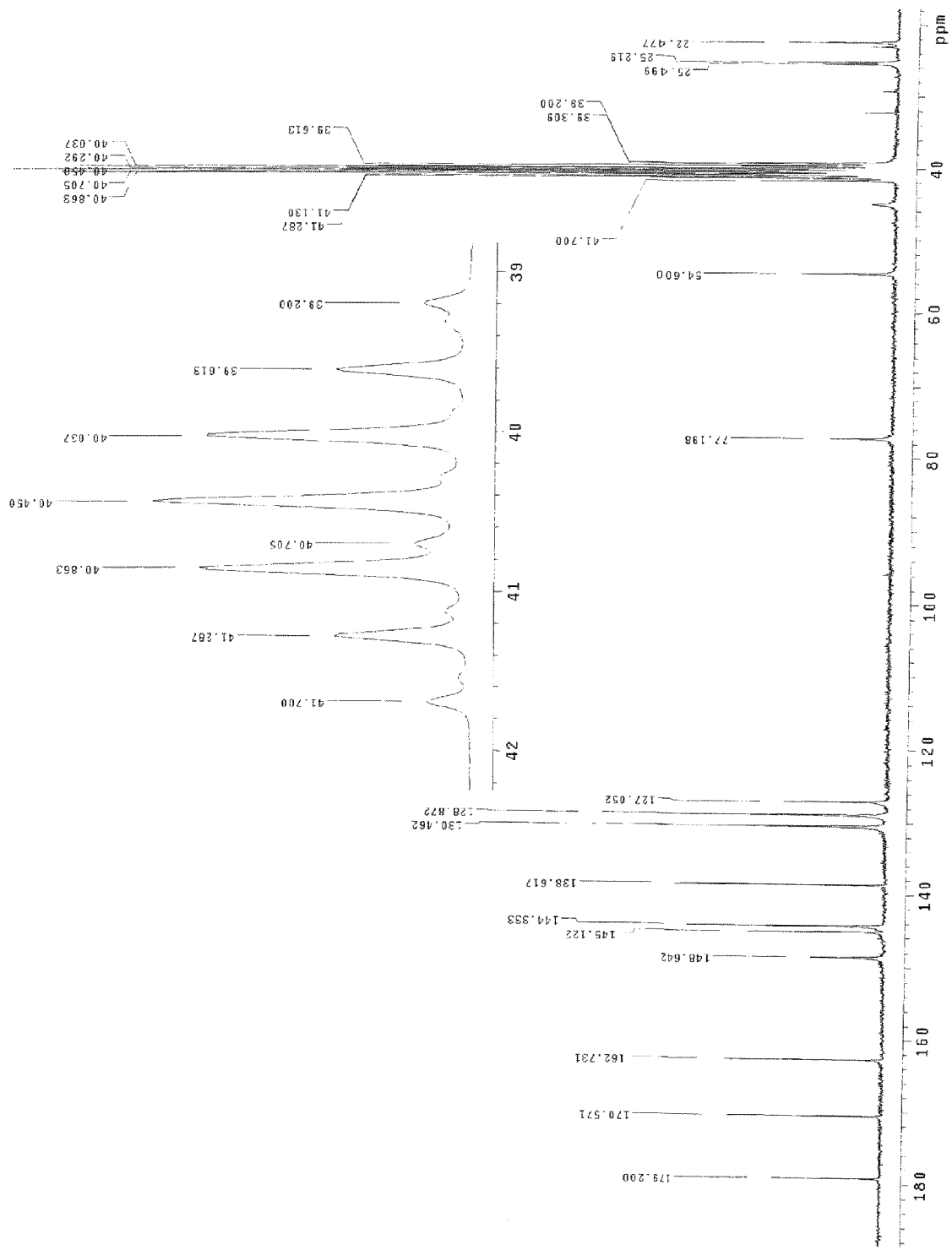
Figure 6:
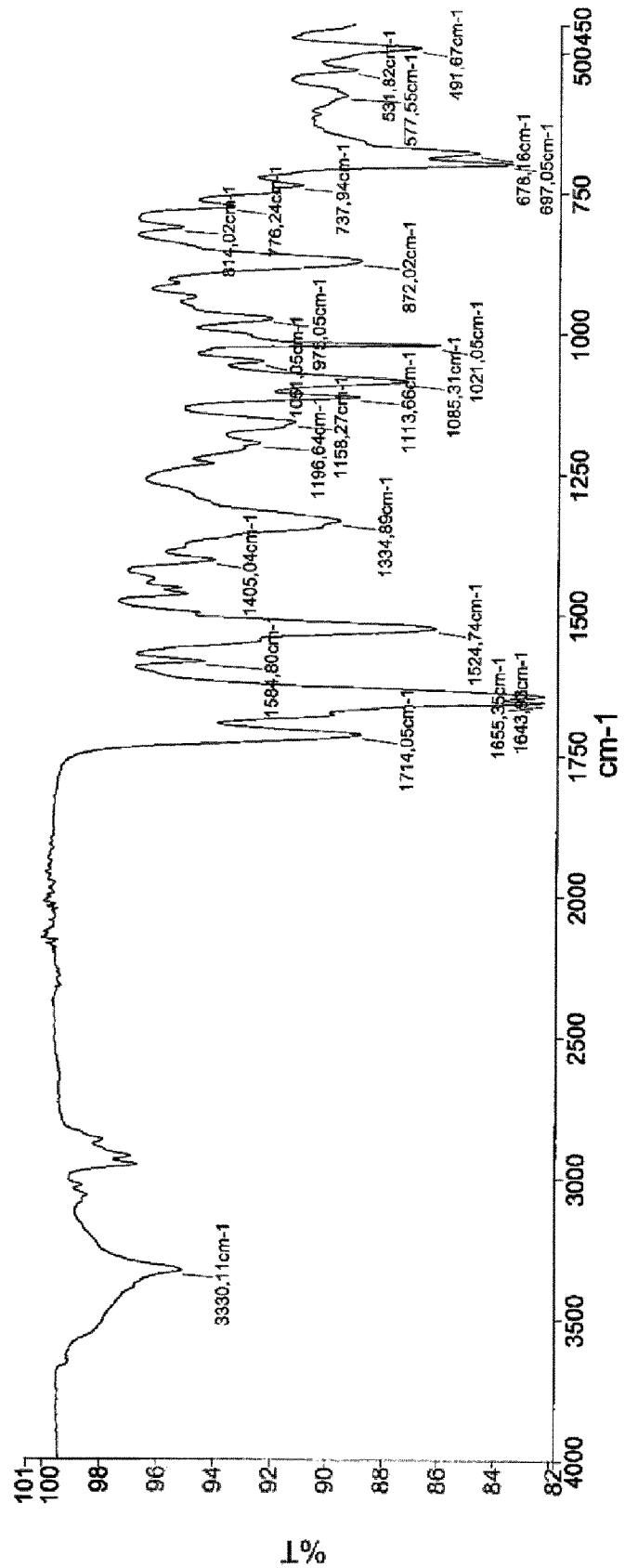

In a 250 ml flask, 2.0 g bortezomib as boroxine were charged and dissolved in 40 ml methanol. Then a solution of 1.2 g disodium L-tartrate in 10 ml water was prepared and such solution was added dropwise in 10 minutes to the methanolic solution of bortezomib, obtaining a solution which was concentrated under vacuum (30 mmHg) at 50° C. up to a solid, which was collected and dried for 10 hours at 50° C., obtaining 3.0 g of product. Such product was then re-suspended in 50 ml acetone and heated under reflux (55° C.). Then the resultant mixture was filtered on gooch to remove the unreacted tartrate which was separated as a solid and the filtrate was heated again under reflux. Then, 25 ml acetone was distilled off and the mixture was cooled to room temperature. The obtained suspension was cooled at 5° C. and kept under these conditions for 2 hours, then filtered on gooch to obtain 2.0 g of wet product, which was dried at 50° C. for 24 hours. In this way 1.4 g of the desired product were obtained. In FIGS. 4, 5 and 6 the $^1$H-NMR, $^{13}$C-NMR and IR spectra, respectively, of the resultant product are reported.

MS ESI ionization in positive: (M+H$^+$) 848.13 (2%), (M+Na+) 869, (100%); ionization in negative: 846 (M−1) (100%).

EXAMPLE 2

Preparation of (5+5) Bis-Bortezomib L-Tartrate III from L-Tartaric Acid

Figure 7:
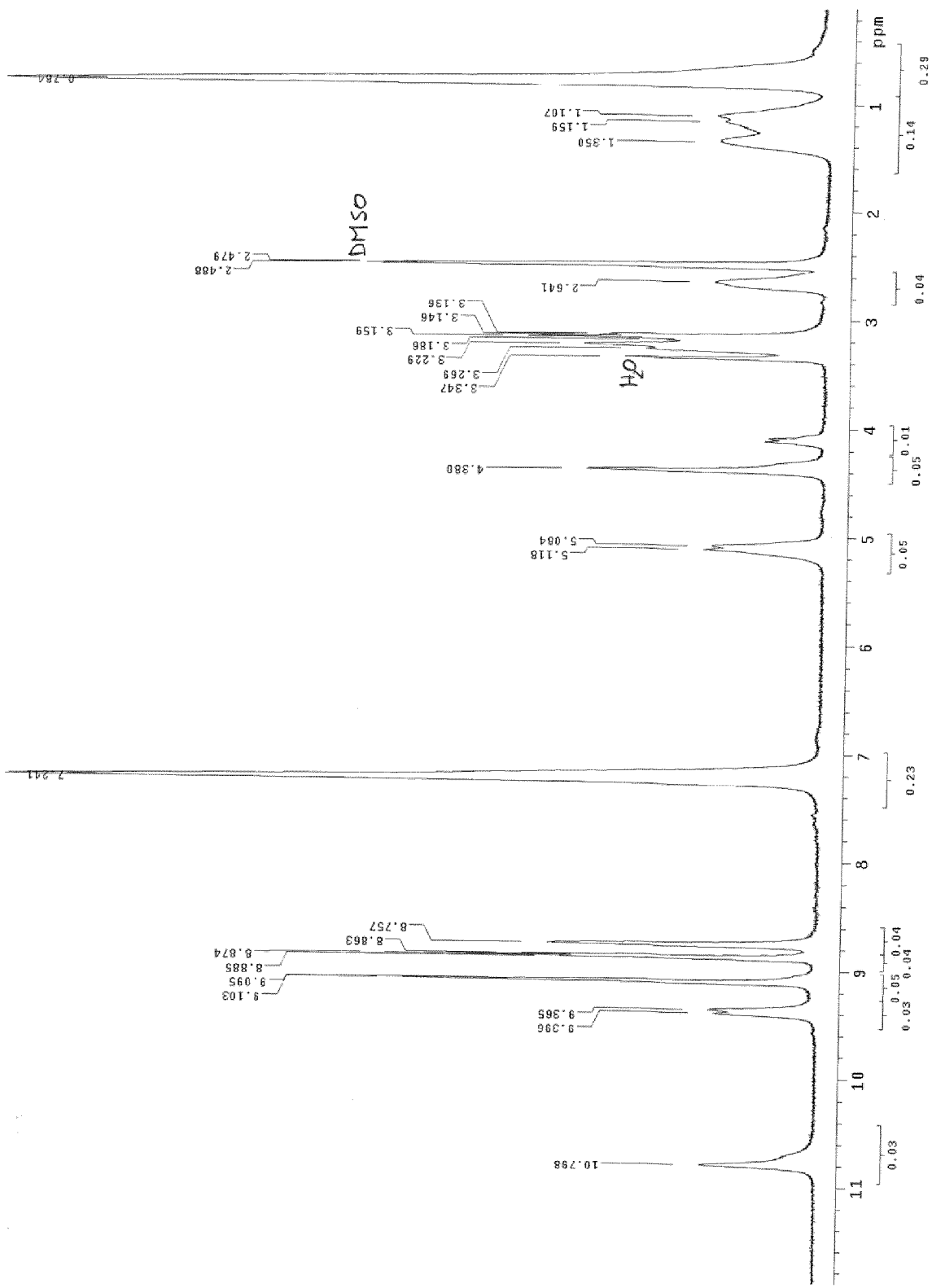
Figure 8:
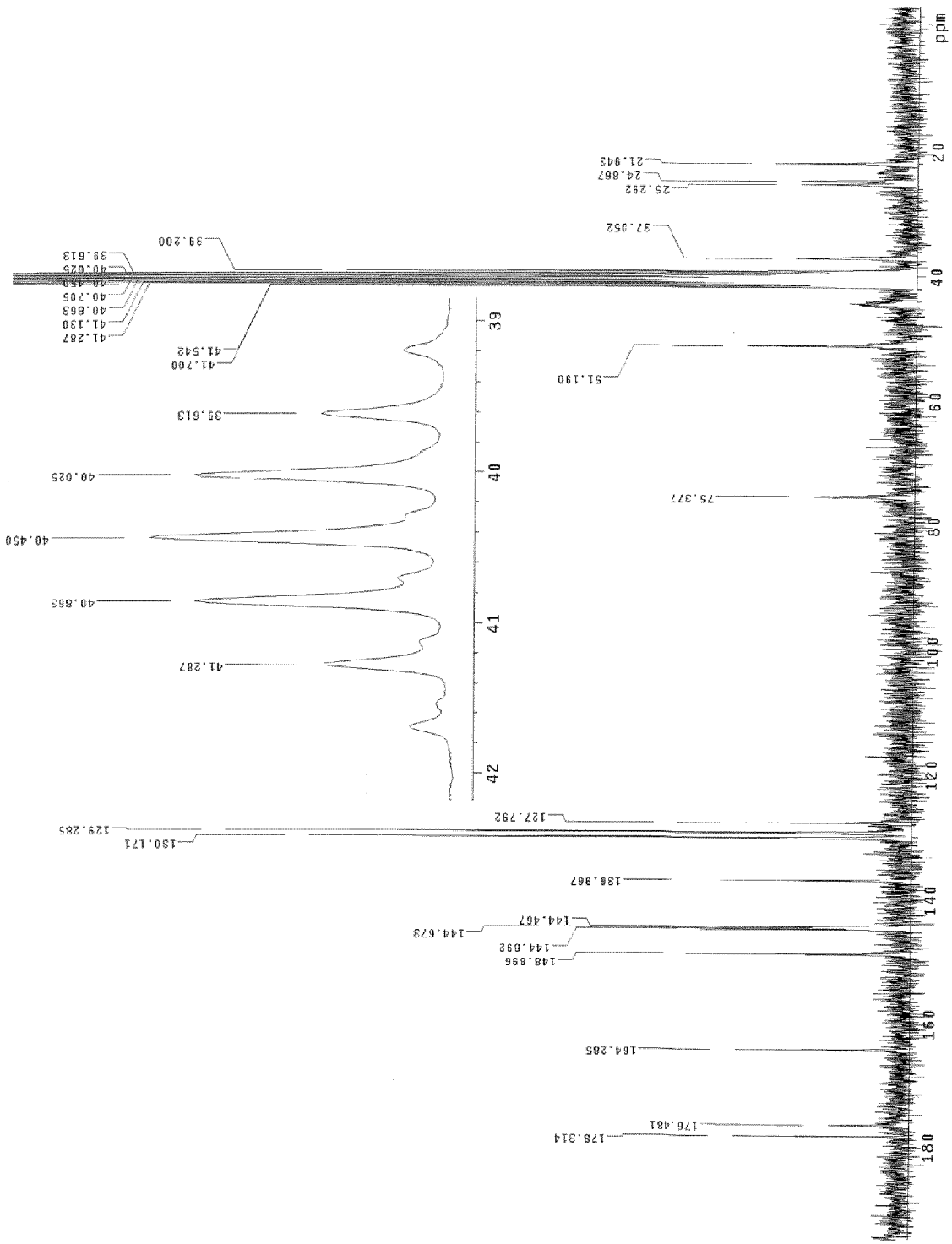
Figure 9:
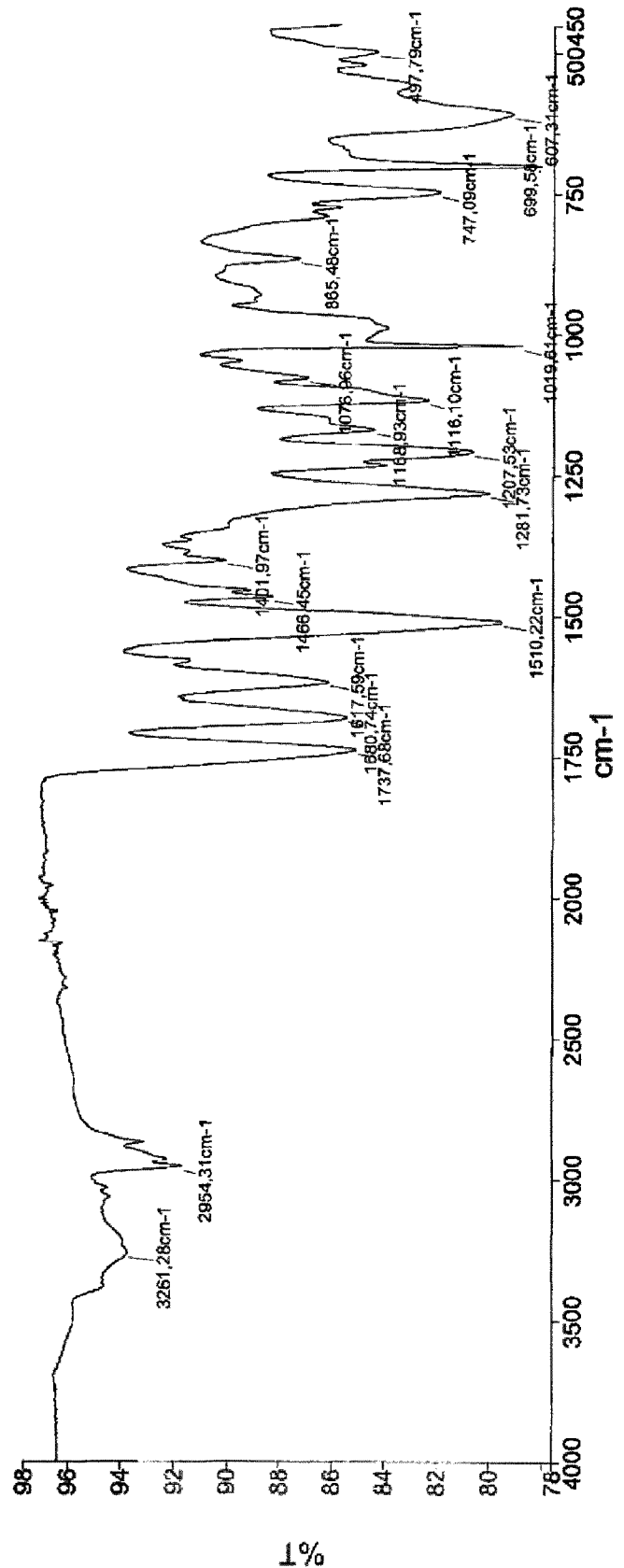

In a 500 ml flask, 10.0 g bortezomib as boroxine and 1.9 g L-tartaric acid were charged and dissolved in 250 ml methanol. Then the mixture was concentrated under vacuum (30 mmHg) at 50° C. up to a solid, which was collected and dried for 10 hours at 45° C. and 1 mmHg, obtaining 12.0 g of product. Such product was then re-dissolved in 50 ml acetone and this solution was added dropwise in 2 hours to 400 ml n-heptane under stirring at 25° C. During the addition a white solid precipitated. The mixture was kept under stirring for 3 hours at 25° C. and then filtered on gooch, obtaining 13.0 g of wet product. This product was dried at 50° C. for 18 hours, obtaining 9.4 g of the desired product. In FIGS. 7, 8 and 9 the $^1$H-NMR, $^{13}$C-NMR and IR spectra, respectively, of the resultant product are reported.

MS ESI ionization in positive: (M+H$^+$) 848.13 (2%), (M+Na+) 869, (100%); ionization in negative: 846 (M−1) (100%).

Figure 10:
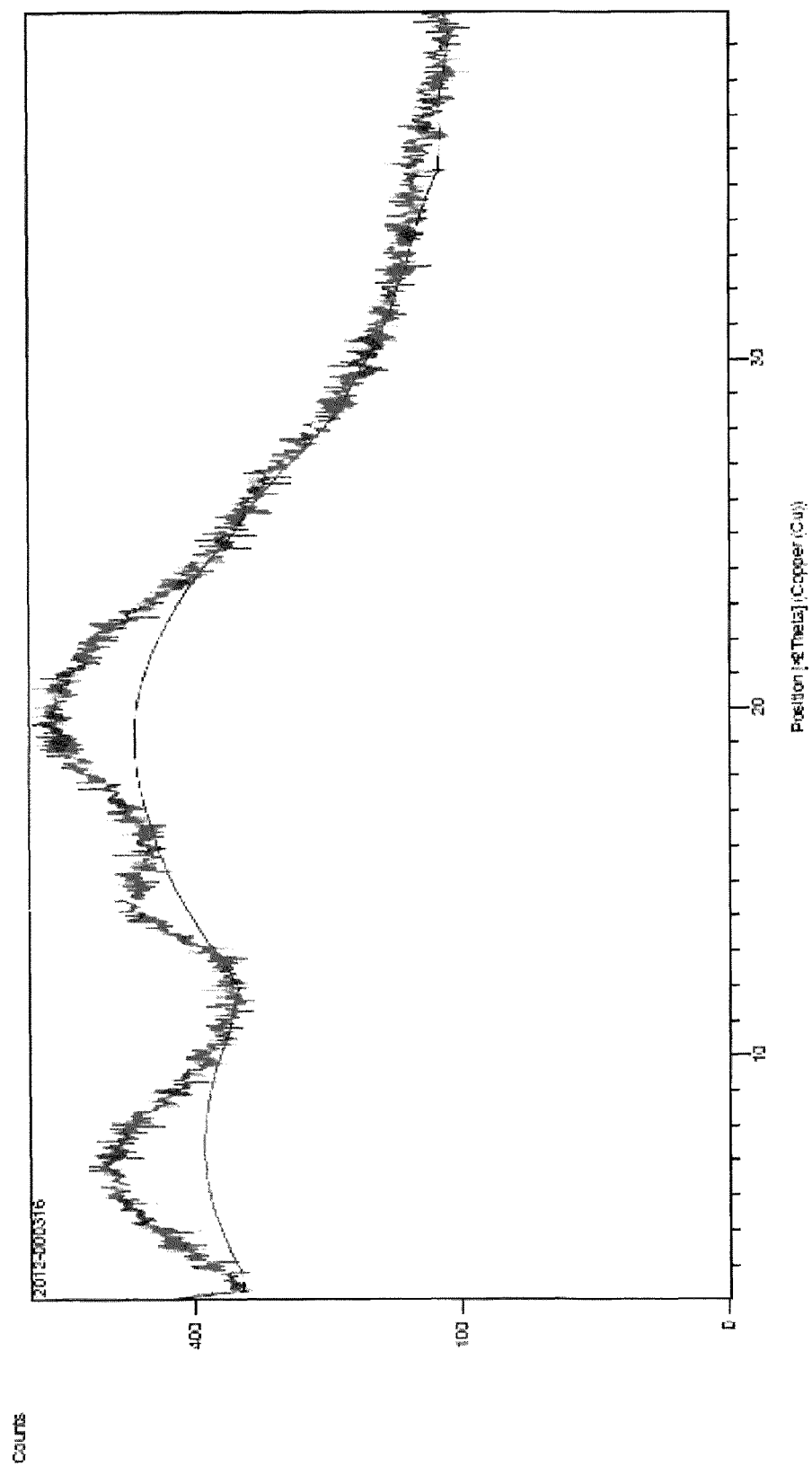

In FIG. 10 the graph related to the PXRD diffractogram of the resultant product is reported.

EXAMPLE 3

Preparation of (5+5) Bis-Bortezomib L-Tartrate III in Admixture with Monobasic Phosphate-Dibasic Phosphate 100 mg of the product prepared as described in example 2, 150 mg anhydrous monobasic sodium phosphate and 850 mg anhydrous dibasic sodium phosphate were charged into a mortar. The powders were mixed in the mortar for 5 minutes up to obtain an uniform white product. The resultant product, dissolved at 1% into a 0.9% NaCl aqueous solution, showed a dissolution time of about 120 seconds. The pH of the resultant solution was 7.5.

EXAMPLE 4

Preparation of (5+5) Bis-Bortezomib L-Tartrate III in Admixture with Monobasic Phosphate-Dibasic Phosphate 100 mg of the product prepared as described in example 2, 350 mg anhydrous monobasic sodium phosphate and 650 mg anhydrous dibasic sodium phosphate were charged into a mortar. The powders were mixed in the mortar for 5 minutes up to obtain a uniform white product. The resultant product, dissolved at 1% into a 0.9% NaCl aqueous solution, showed a dissolution time of about 120 seconds. The pH of the resultant solution was 6.8.

EXAMPLE 5

Preparation of (6+6) Bis-Bortezomib L-Tartrate IV in Crystalline Form A

In a 250 ml flask, 2.0 g bortezomib as boroxine were charged and dissolved in 40 ml methanol. Then a solution of 0.6 g disodium L-tartrate in 10 ml water was prepared and such solution was added dropwise in 10 minutes to the methanolic solution of bortezomib, obtaining a solution which was concentrated under vacuum (30 mmHg) at 50° C. up to a solid, which was collected and dried for 10 hours at 50° C., obtaining 2.1 g of product. Such product was then re-suspended in 5 ml acetone and heated under reflux (55° C.). The resultant mixture became a solution. Then 10 ml n-heptane were added dropwise. The obtained suspension was cooled at 25° C. and kept under these conditions for 2 hours, then filtered on gooch to obtain 1.5 g of wet product, which was dried at 50° C. for 24 hours.

Figure 11:
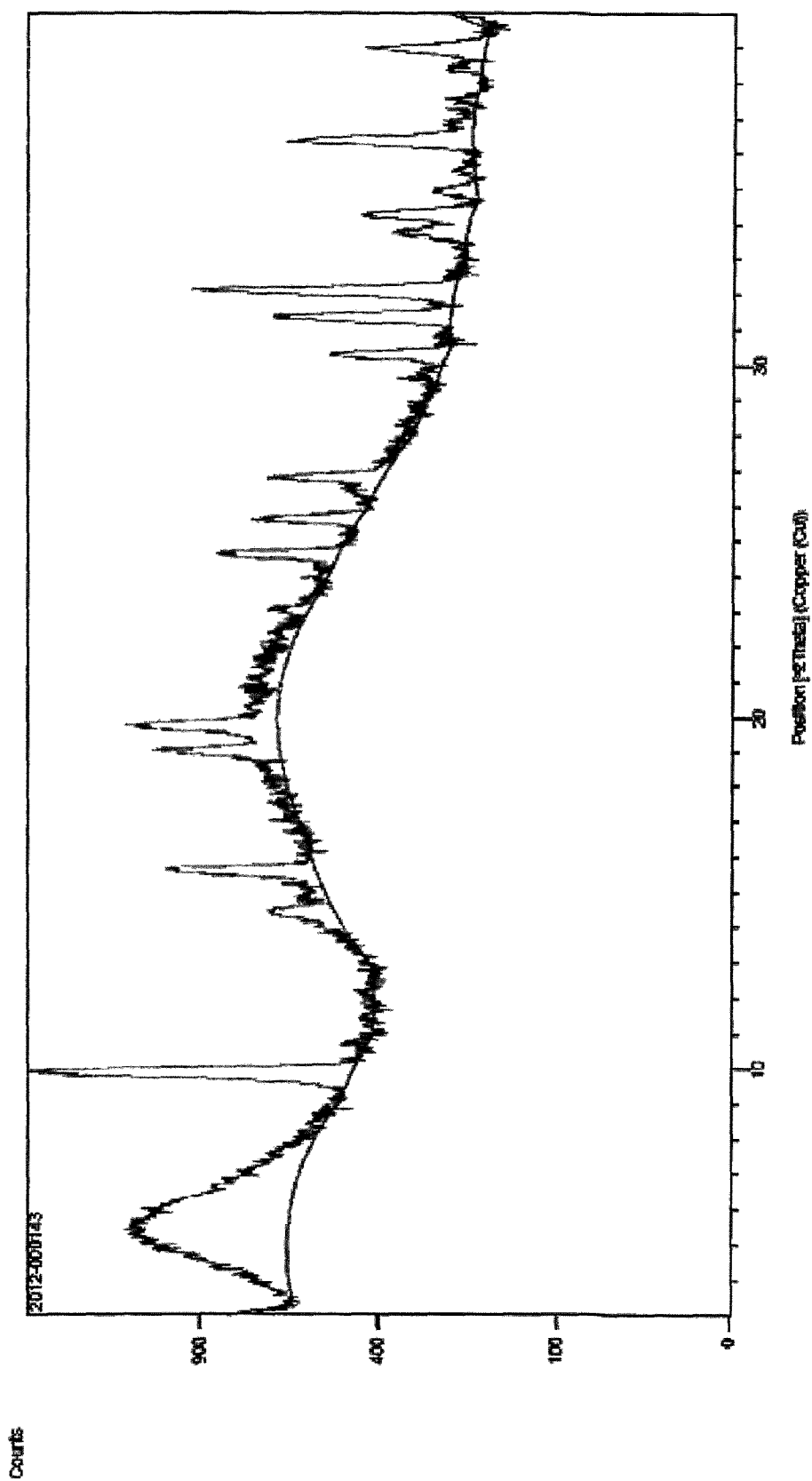

In FIG. 11 the graph related to the PXRD diffractogram of the resultant product is reported.

EXAMPLE 6

Preparation of (6+6) bis-bortezomib L-tartrate IV in crystalline form B In a 250 ml flask, 2.5 g bortezomib as boroxine were charged and dissolved in 50 ml methanol. Then a solution of 0.75 g disodium L-tartrate in 10 ml water was prepared and such solution was added dropwise in 10 minutes to a methanolic solution of bortezomib, obtaining a solution which was concentrated under vacuum (30 mmHg) at 50° C. up to a solid, which was collected and dried for 10 hours at 50° C., obtaining 3.0 g of product. Such product was then re-suspended in 33 ml acetone and heated under reflux (55° C.). The resultant mixture became a solution. Then 65 ml n-heptane were added dropwise. The obtained suspension was cooled at 25° C. and kept under these conditions for 2 hours, then filtered on gooch to obtain 4.2 g of wet product, which was dried at 50° C. for 24 hours.

Figure 12:
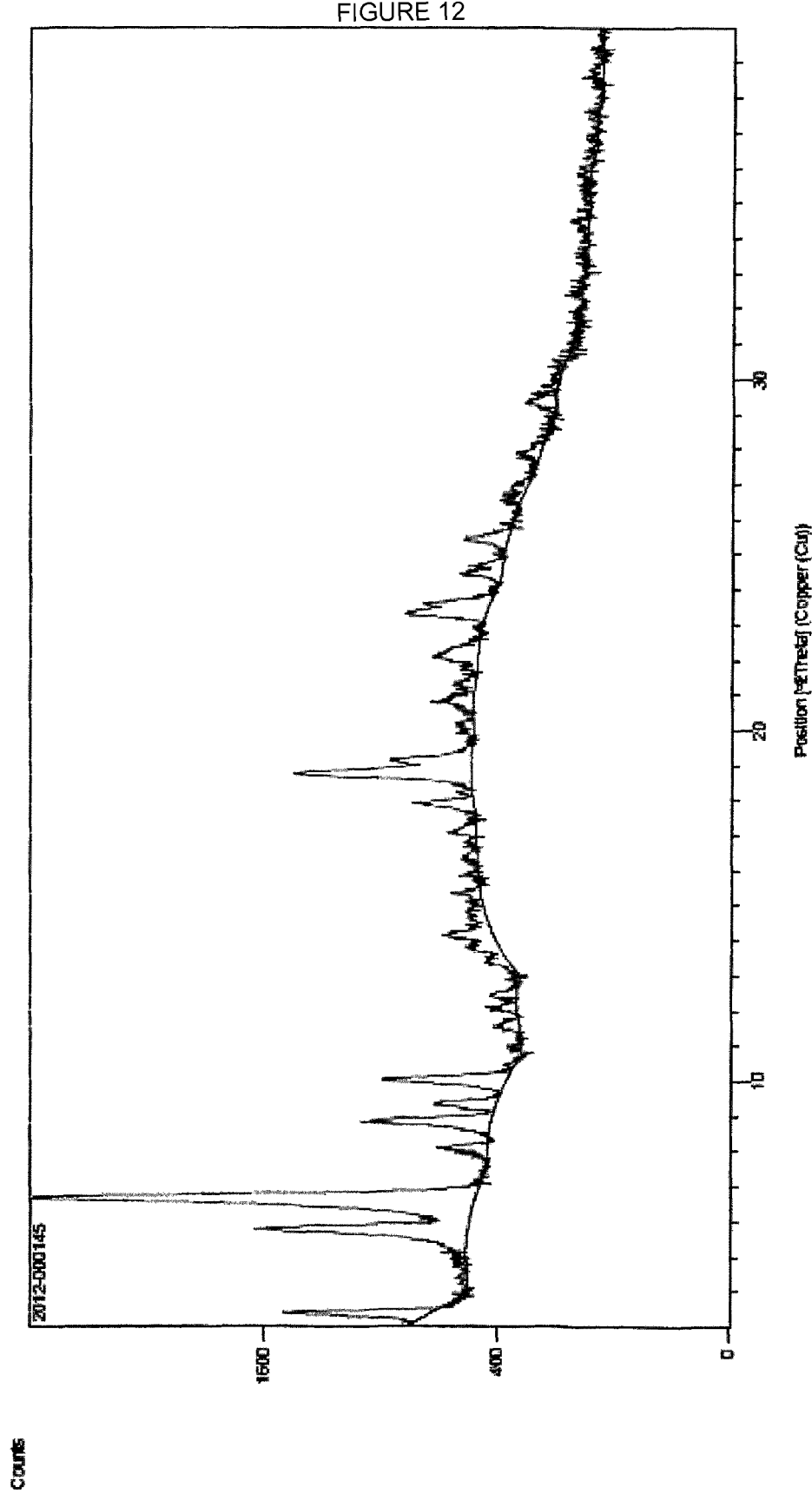

In FIG. 12 the graph related the PXRD diffractogram of the resultant product is reported.

EXAMPLE 7

Preparation of (6+6) Bis-Bortezomib L-Tartrate IV in Amorphous Form

In a 250 ml flask, 2.0 g bortezomib as boroxine were charged and dissolved in 40 ml methanol. Then a solution of 0.6 g disodium L-tartrate in 10 ml water was prepared and such solution was added dropwise in 10 minutes to the methanolic solution of bortezomib, obtaining a solution which was concentrated under vacuum (30 mmHg) at 50° C. up to a solid, which was collected and dried for 10 hours at 50° C., obtaining 2.1 g of product. Such product was then re-dissolved in 5 ml acetone and heated under reflux (55° C.). The resultant mixture became a solution and was added dropwise to 40 ml n-heptane in about 30 minutes. The suspension was kept under stirring at 25° C. for 2 hours, then filtered on gooch to obtain 3.8 g of wet product, which was dried at 50° C. for 24 hours.

Figure 13:
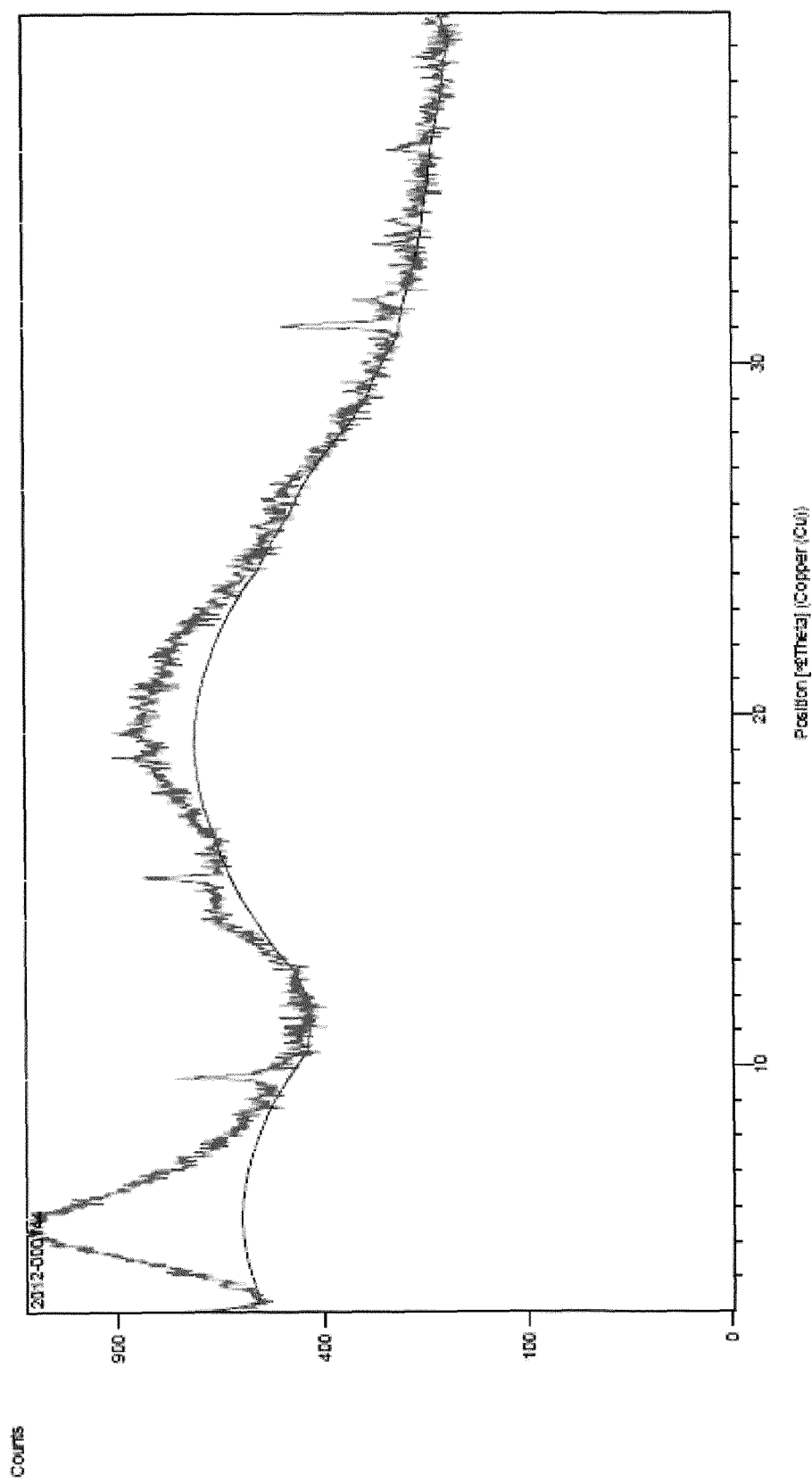
Figure 14:
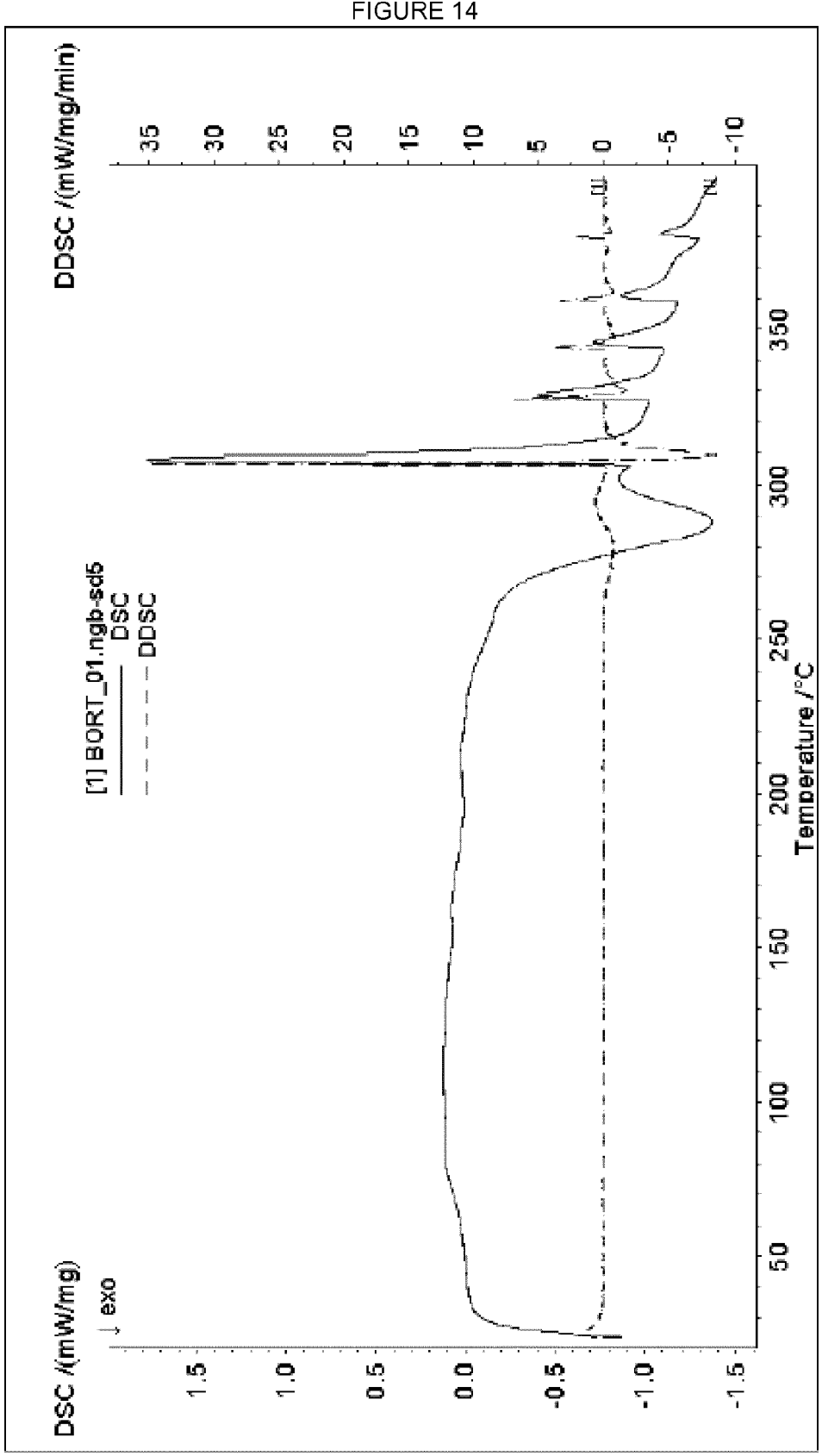

In FIG. 13 the graph related to the PXRD diffractogram of the resultant product is reported.

EXAMPLE 8

Preparation of (5+5) bis-bortezomib D-tartrate III from D-tartaric acid

In a 250 ml flask 5.0 g bortezomib as boroxine and 0.95 g D-tartaric acid were charged and dissolved in 120 ml methanol. The mixture was concentrated under vacuum (30 mmHg) at 50° C. up to a solid which was collected and dried for 10 hours at 45° C. and 1 mmHg, obtaining 12.0 g product. Such product was then re-dissolved in 25 ml acetone; this solution was added dropwise in 2 hours to 200 ml n-heptane under stirring at 25° C. During the addition a white solid precipitated. The mixture was kept under stirring for 3 hours at 25° C. and then filtered on gooch, obtaining 6.2 g of wet product. This was dried at 50° C. for 18 hours obtaining 4.8 g of the desired product.

EXAMPLE 9

Stability Tests of (5+5) Bis Bortezomib Tartrate III in Solid Form (5+5) Bis-bortezomib tartrate III, prepared as described in example 2, and the solid formulations containing (5+5) bis-bortezomib tartrate III, prepared as described in examples 3 and 4, were put into glass vials with screw plug and hermetic closure and undergone stability tests under the following conditions:
temperature 25° C. and 60% relative humidity
temperature 40° C. and 75% relative humidity
The HPLC method used for the purity analysis was the following:
Operative Conditions
Instrument: HPLC SHIMADZU LC-10AD
  UV Detector: SPD 10AVP
  auto-sampler: SIL-ADVP
Wavelength: 270 nm
Column: Biobasic-18-Peek Bio-inert
  length: 250 mm
  I.D.: 2.1 mm
  Particle size: 5 μm
  (thermo scientific Cat.N.72105-252168 or equivalent)
Injection: 3 μl
Column temperature: room
Sampler temperature: room
Flow rate: 0.3 ml/min
Mobile phase: eluent A: 95% gradient
  Eluent B: 5%
Analysis time: 60 minutes
Eluent A: 0.1% v/v formic acid in water for HPLC
Eluent B: 0.1% v/v formic acid in acetonitrile for gradient
Diluent: acetonitrile:water for HPLC=80:20
Blank: diluent
Gradient program:

| Time (min) | Eluent A % (v/v) | Eluent B % (v/v) |
|---|---|---|
| 0 | 95 | 5 |
| 10 | 95 | 5 |
| 40 | 20 | 80 |
| 45 | 20 | 80 |
| 46 | 95 | 5 |
| 60 (run end) | 95 | 5 |

Sample Solution:
Weigh about 50 mg sample and transfer the substance into a 100 ml flask. Dissolve and bring to volume with diluent. Sonicate up to complete dissolution (analyte content about 0.5 mg/ml).

Purity Calculation
Calculate the percentage of each known and unknown impurity as percentage area by using the following formula (peaks of the blank and peaks with area <0.05% to be ignored).

$$\% \text{ impurity} = \frac{A_{xc} * 100}{A_{tot}}$$

$A_{xc}$: peak area of the impurity in the sample
$A_{tot}$: total area of the peaks of the chromatogram $$\text{Purity}(A\%) = 100 - \Sigma_1 Imp \qquad (i)$$

The peak corresponding to bortezomib is eluted at 28 minutes±2.

In the following tables the data obtained from the stability tests after two and four weeks are reported.

| | | Retention time (min) | | | | | |
|---|---|---|---|---|---|---|---|
| | | 23.58 | 24.57 | 25.78 | 27.00 | 28.00 | 28.77 |
| | | \multicolumn{6}{c}{Relative retention time} | | | | | |
| | Sample | 0.87 | 0.91 | 0.95 | 1.00 | 1.037 | 1.07 |
| Example 2 | t0 | | 0.02 | 0.07 | 99.90 | NQ | 0.01 |
| | 2 weeks 25° C. | | 0.02 | 0.02 | 99.94 | NQ | 0.01 |
| | 2 weeks 40° C. | | | 0.18 | 99.82 | NQ | 0.01 |

| | | Retention time (min) | | | | | | |
|---|---|---|---|---|---|---|---|---|
| | | 23.58 | 24.57 | 25.37 | 25.78 | 27.00 | 28.00 | 28.77 |
| | | \multicolumn{7}{c}{Relative retention time} | | | | | | |
| | Sample | 0.87 | 0.91 | 0.94 | 0.95 | 1.00 | 1.037 | 1.07 |
| example 3 | t0 | | 0.04 | 0.01 | | 99.93 | NQ | 0.02 |
| | 2 weeks 25° C. | 0.02 | 0.05 | | | 99.89 | NQ | 0.04 |
| | 2 weeks 40° C. | | | 0.04 | 0.05 | 99.86 | NQ | 0.04 |
| | 4 weeks 25° C. | 0.01 | 0.01 | 0.02 | 0.03 | 99.90 | NQ | 0.03 |
| | 4 weeks 40° C. | 0.04 | | | 0.25 | 99.63 | 0.03 | 0.05 |
| example 4 | t0 | | | 0.01 | | 99.97 | NQ | 0.02 |
| | 2 weeks 25° C. | | | 0.01 | 0.04 | 99.90 | NQ | 0.03 |
| | 2 weeks 40° C. | | | 0.02 | 0.12 | 99.83 | NQ | 0.04 |
| | 4 weeks 25° C. | 0.01 | | | 0.01 | 99.94 | NQ | 0.04 |
| | 4 weeks 40° C. | 0.04 | | | 0.15 | 99.77 | NQ | 0.04 |

EXAMPLE 10

Stability Tests of (5+5) Bis Bortezomib Tartrate III in Solution 3.8 g (5+5) bis-bortezomib tartrate III, prepared as described in example 2, were dissolved in 100 ml DMSO (mother solution). An aliquot of 1 ml of such solution was diluted with 1 ml DMSO.

The mother solution (38 g/l) and the diluted 1:1 solution (19 g/l) were put into glass vials with screw cap and hermetic closure and undergone stability tests under the following conditions:

temperature 25° C. and 60% relative humidity
temperature 40° C. and 75% relative humidity.

In the following table the data obtained from the stability tests after two weeks are reported.

The HPLC method used for the purity analysis was the same as described in example 9.

| | | Retention time (min) | | | | | |
|---|---|---|---|---|---|---|---|
| | | 23.58 | 24.57 | 25.78 | 27.00 | 28.00 | 28.77 |
| | | | | Relative retention time | | | |
| | Sample | 0.87 | 0.91 | 0.95 | 1.00 | 1.037 | 1.07 |
| Mother solution (38 g/l) | t0 | | | | 99.97 | NQ | 0.03 |
| | 2 weeks 25° C. | | | 0.02 | 99.93 | NQ | 0.05 |
| | 2 weeks 40° C. | | | 0.02 | 99.93 | NQ | 0.05 |
| 1:1 solution 19 g/l | t0 | | | | 99.97 | NQ | 0.03 |
| | 2 weeks 25° C. | 0.01 | | 0.02 | 99.91 | NQ | 0.06 |
| | 2 weeks 40° C. | | | 0.02 | 99.93 | NQ | 0.05 |

EXAMPLE 11

Figure 15A:
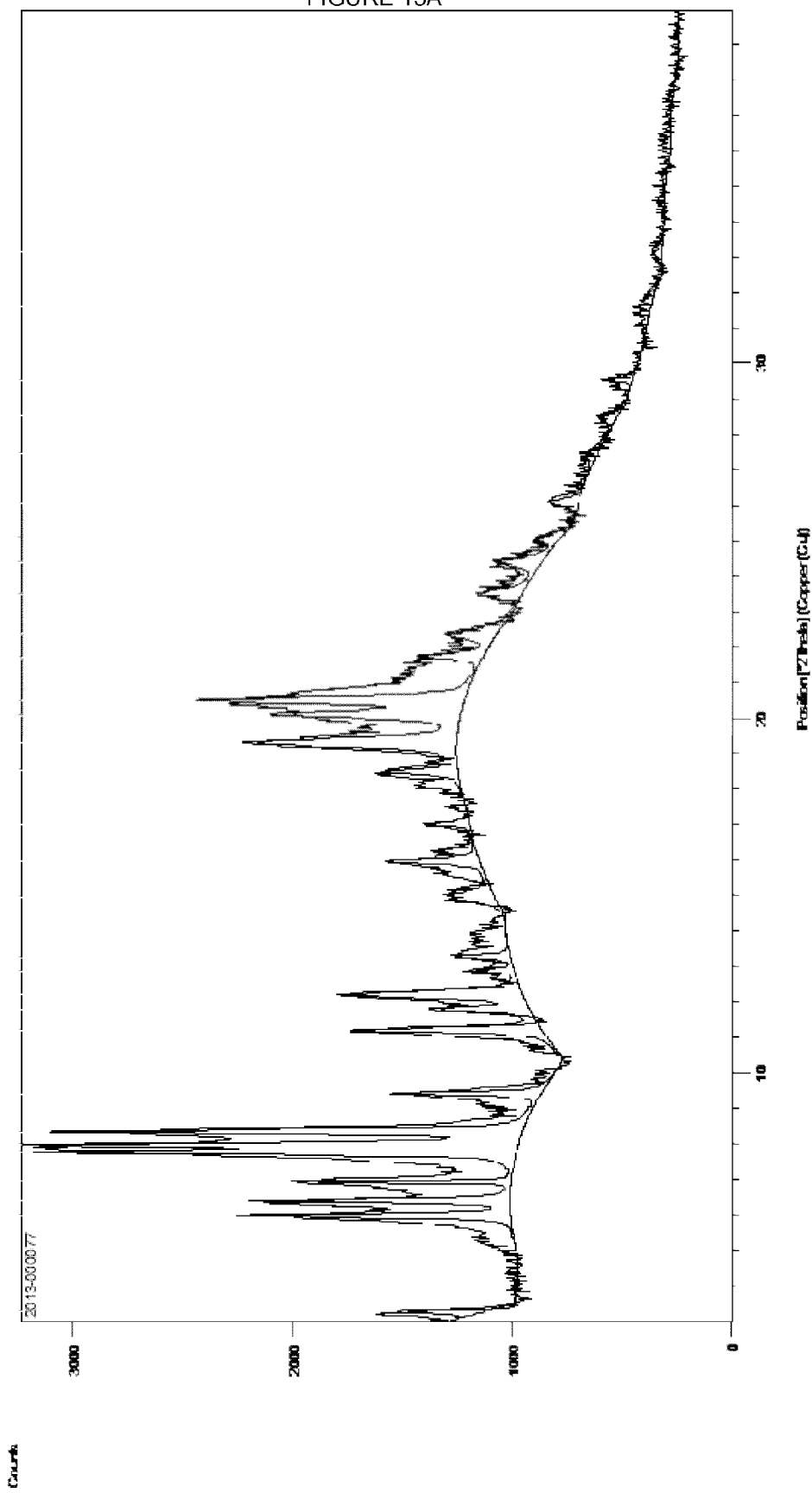

Preparation of (5+5) Bis Bortezomib L-Tartrate III Crystalline Form A from Acetone/Heptane In a 4-neck 250 ml flask, equipped with mechanical stirrer, thermometer and cooler, 5.0 g bortezomib-boroxine, 0.95 g L tartaric acid and 50 ml acetone were charged. The mixture was heated to 45° C. under stirring and under nitrogen, obtaining complete dissolution of the solid after 5 minutes. The reaction mixture was kept under these conditions for 1 hour, then was cooled to 20-25° C. and poured onto 200 m I n-heptane in about 1 hour. The development of a gummy white solid was observed which tended to become powder in 2 hours. After keeping for 18 hours under stirring at 20-25° C., it was filtered on gooch and washed with 20 ml n-heptane. 6.9 g of wet product were obtained. After drying for 24 hours at 50° C. and 30 mmHg, 4.8 g of dry product were obtained which show the PXRD reported in FIG. 15.

EXAMPLE 12

Stability Tests of (5+5) Bis Bortezomib L-Tartrate III Crystalline Form A from Acetone/Heptane Samples of the powder obtained in example 11 were stored in glass vials with screw cap and hermetic closure and undergone stability tests at 40° C. and 75% relative humidity. Their purity was checked during the time. In the following table the purity data of the samples under stability test obtained by using the HPLC method described in example 9 are reported.

| | Retention time (min) | | | | | |
|---|---|---|---|---|---|---|
| | 23.58 | 24.57 | 25.78 | 27.00 | 28.00 | 28.77 |
| | | | Relative retention time | | | |
| Sample | 0.87 | 0.91 | 0.95 | 1.00 | 1.037 | 1.07 |
| t0 | | | | 99.99 | 0.01 | |
| 2 months 40° C. | 0.15 | | | 99.67 | 0.02 | 0.04 |
| 3 months 40° C. | 0.66 | | 0.07 | 98.72 | 0.38 | 0.18 |

EXAMPLE 13

Preparation of (5+5) Bis Bortezomib L-Tartrate III Amorphous Form from Ethyl Acetate/MTBE In a 4-neck 250 ml flask, equipped with mechanical stirrer, thermometer and cooler, 5.1 g bortezomib-boroxine, 0.97 g L tartaric acid and 50 ml ethyl acetate were charged. The mixture was heated to 45° C. under stirring and under nitrogen, obtaining partial dissolution of the solid after 5 minutes. The reaction mixture was kept at 45° C. for 1 hour without reaching complete dissolution. Then 200 ml MTBE were added in about 1 hour, the reaction mixture was cooled to 20-25° C. and kept under stirring for 18 hours. It was filtered on gooch and washed with 20 ml MTBE. 6.5 g of wet product were obtained. After drying for 18 hours at 50° C. and 30 mmHg, 4.4 g of dry product were obtained which show PXRD similar to those reported in FIG. 10.

EXAMPLE 14

Stability Tests of (5+5) Bis Bortezomib L-Tartrate III Amorphous Form from Ethyl Acetate/MTBE Samples of the powder obtained in example 13 were stored in glass vials with screw cap and hermetic closure and undergone stability tests at 40° C. and 75% relative humidity. In the following table the purity data obtained by using the HPLC method described in example 9 are reported.

| | Retention time (min) | | | | | |
|---|---|---|---|---|---|---|
| | 23.58 | 24.57 | 25.78 | 27.00 | 28.00 | 28.77 |
| | | | Relative retention time | | | |
| Sample | 0.87 | 0.91 | 0.95 | 1.00 | 1.037 | 1.07 |
| t0 | 0.02 | | | 99.94 | 0.02 | |
| 1 month 40° C. | 0.05 | | | 99.93 | 0.02 | |
| 2 months 40° C. | 0.61 | | 0.07 | 98.85 | 0.34 | 0.13 |
| 3 months 40° C. | 0.07 | | 0.04 | 99.85 | 0.02 | |

EXAMPLE 15

Figure 16A:
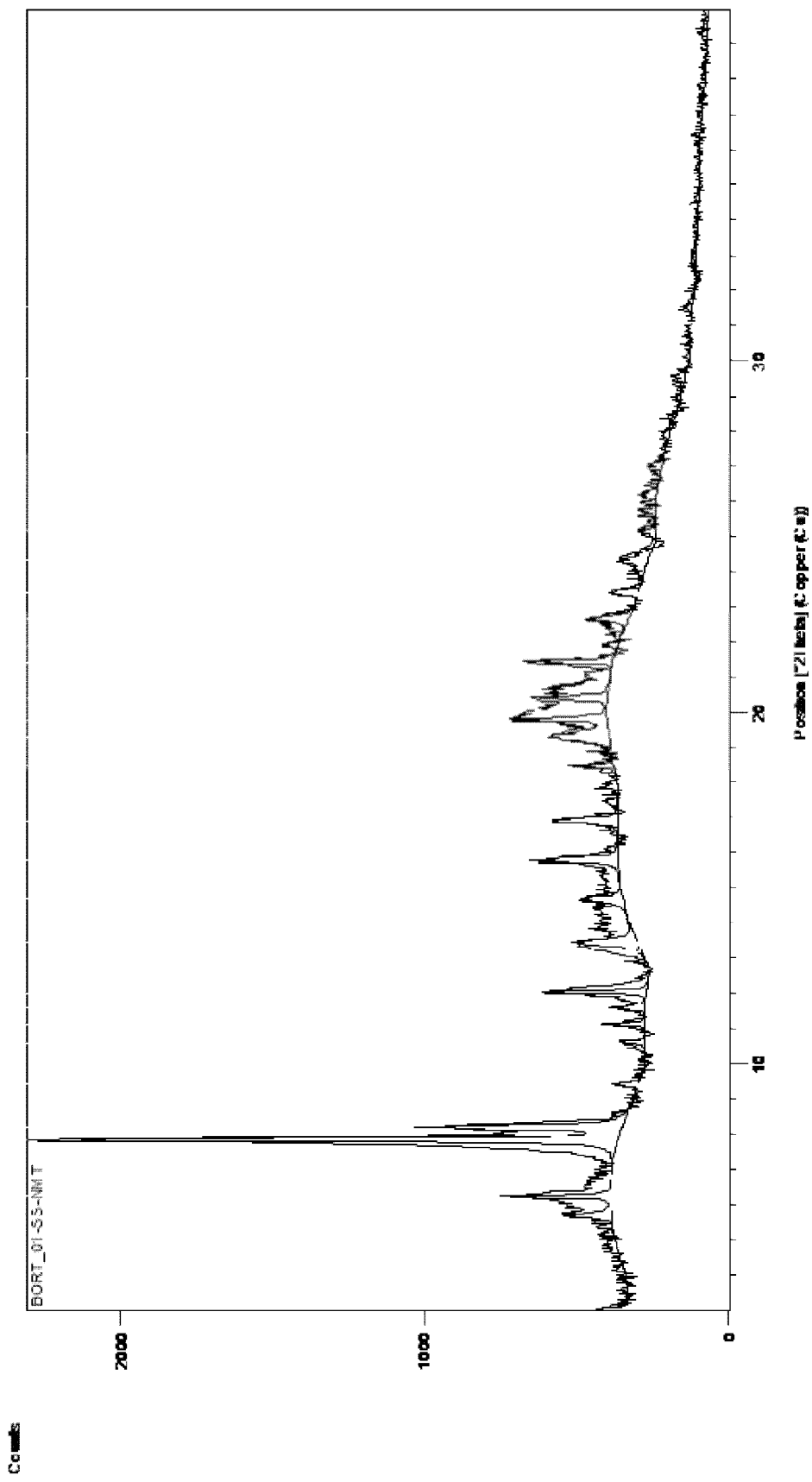
Figure 17:
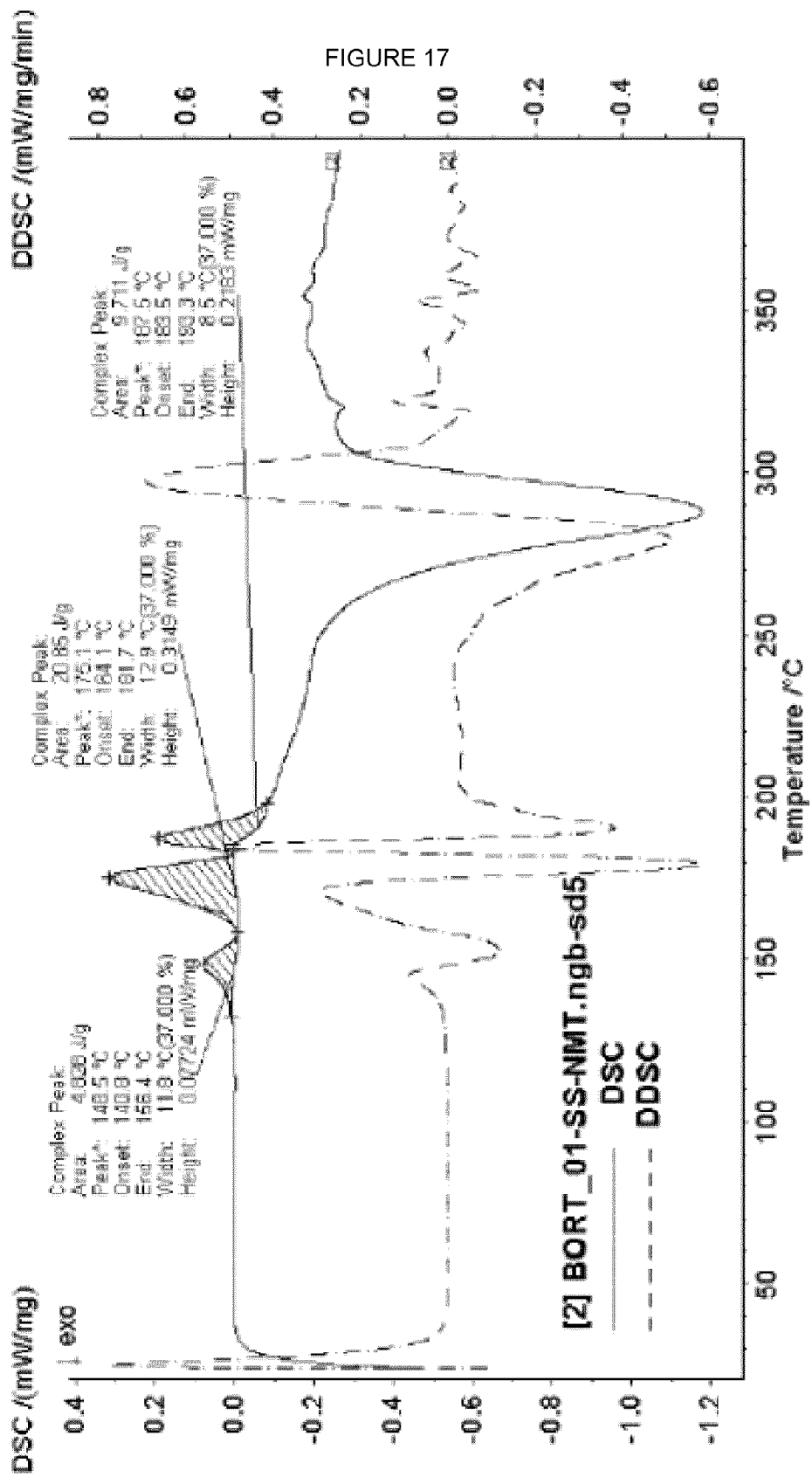

Preparation of (5+5) Bis Bortezomib L-Tartrate III Crystalline Form a from Nitromethane 4 ml nitromethane were saturated at 25° C. with (5+5) bis bortezomib L-tartrate III prepared as described in example 2. The resultant solution was filtered on Whatman 0.45 mm filter and kept at 0-4° C. up to obtain a precipitate. The resultant solid product was filtered on buchner, dried and analyzed by PXRD (FIG. 16) and DSC (FIG. 17).

EXAMPLE 16

Figure 18A:
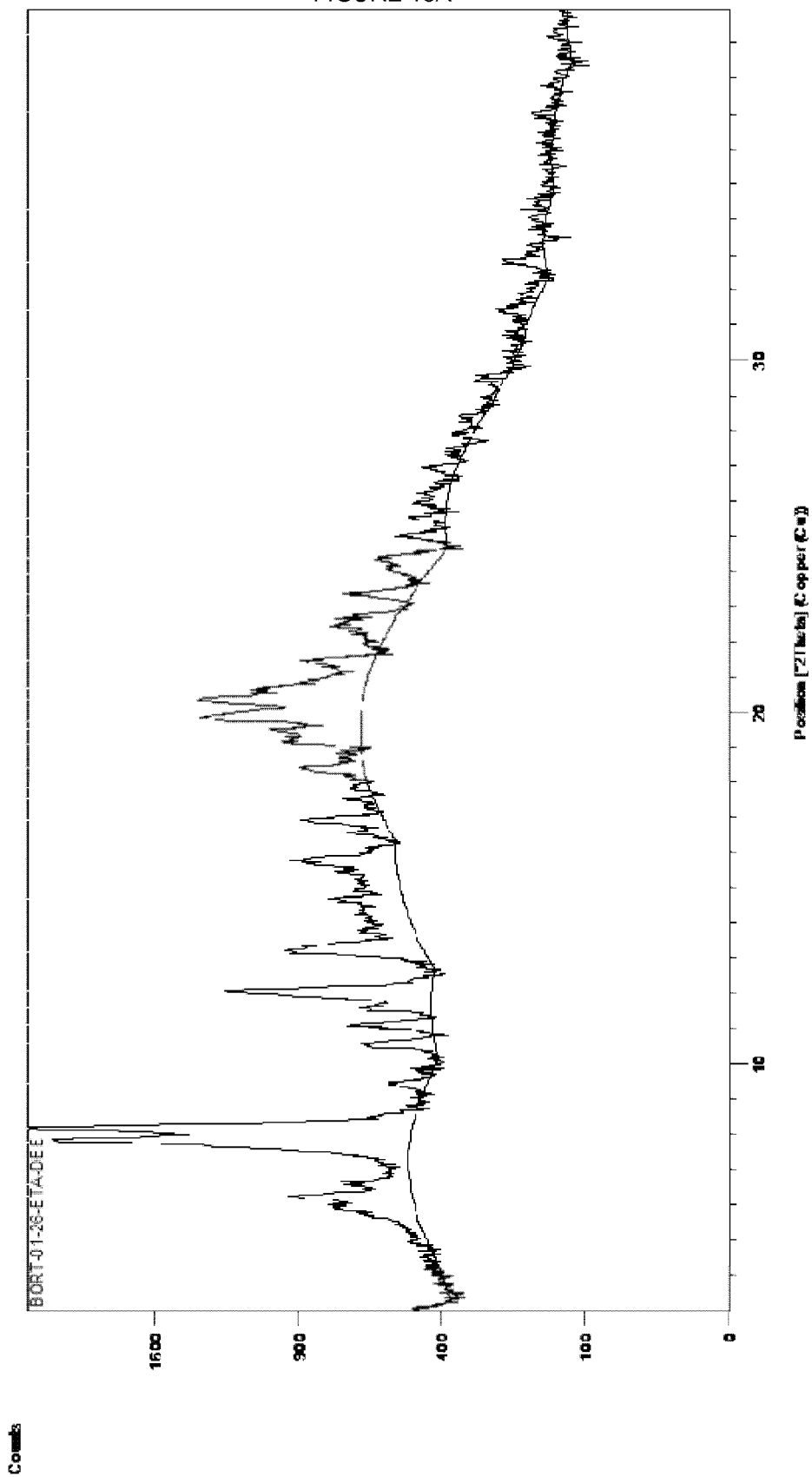
Figure 19:
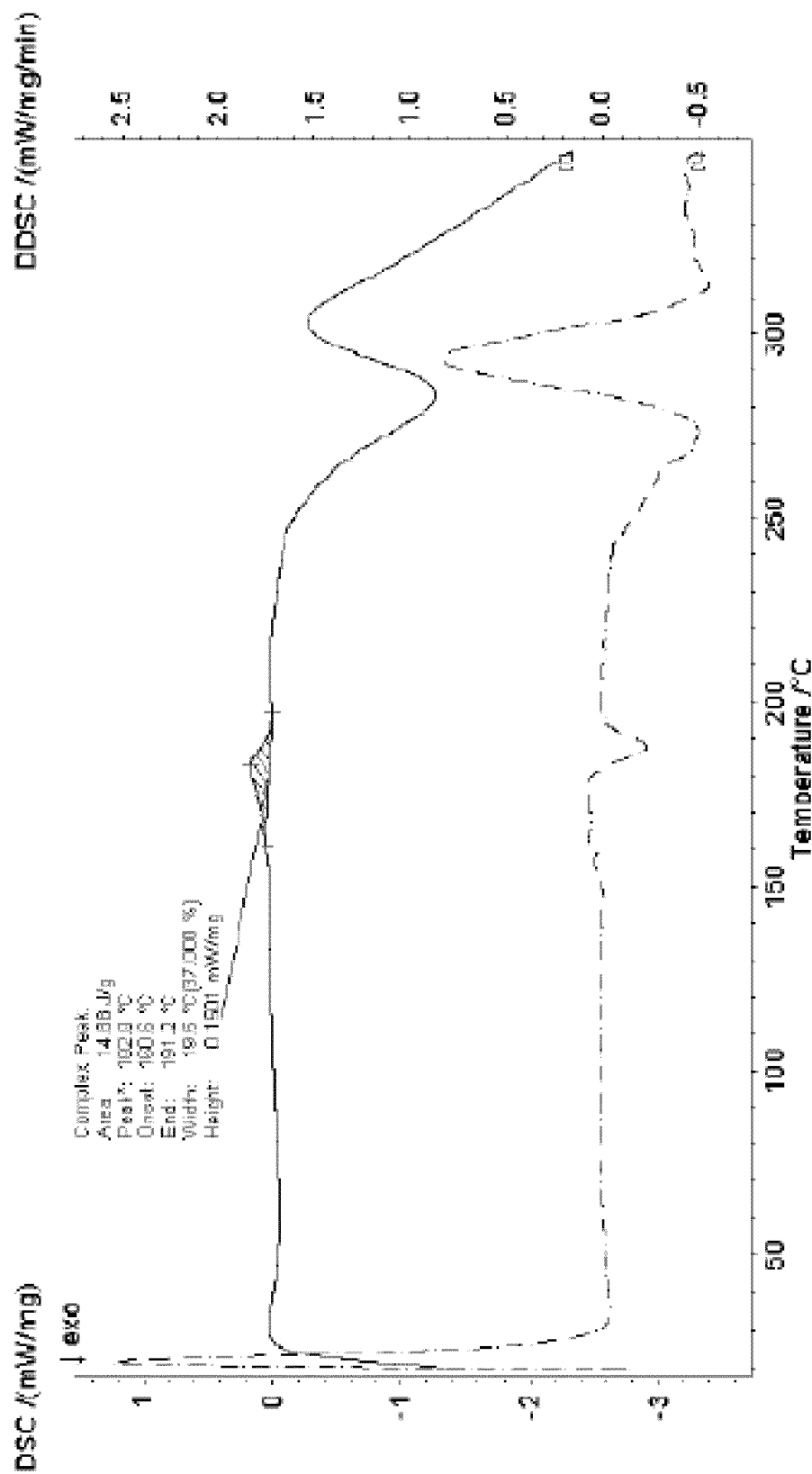

Preparation of (5+5) Bis Bortezomib L-Tartrate III Crystalline Form A from Ethyl Acetate/Diethylether 150 mg (5+5) bis bortezomib L-tartrate III prepared as described in example 2 were dissolved in 2 ml ethyl acetate. The resultant solution was filtered on Whatman 0.45 mm filter and added with 8 ml diethylether up to obtain a precipitate. The resultant solid product was filtered on buchner, dried and analyzed by PXRD (FIG. 18) and DSC (FIG. 19).

EXAMPLE 17

Preparation of (5+5) Bis Bortezomib L-Tartrate III in Admixture with Disodium Tartrate 100 mg (5+5) bis bortezomib L-tartrate III prepared as described in example 2 and 1 g disodium tartrate were weighed in a mortar. The powders were mixed with the pestle into the mortar for 5 minutes up to a uniform white solid mixture. The resultant product, if dissolved at 1% in a 0.9% NaCl aqueous solution, showed a dissolution time of about 120 seconds. The pH of the resultant solution was 5.2.

In the following table the data of the HPLC purity analysis of the powder at time 0 and after 1 month, 2 months and 3 months of storage in glass vials with screw plug and hermetic closure at 40° C. are reported.

|  | Retention time (min) | | | | | |
| --- | --- | --- | --- | --- | --- | --- |
|  | 23.58 | 24.57 | 25.78 | 27.00 | 28.00 | 28.77 |
|  | | | Relative retention time | | | |
| Sample | 0.87 | 0.91 | 0.95 | 1.00 | 1.037 | 1.07 |
| t0 | | | | 99.99 | 0.01 | |
| 1 month 40° C. | 0.07 | | | 99.93 | | |
| 2 months 40° C. | 0.05 | | 0.08 | 99.86 | 0.01 | |
| 3 months 40° C. | 0.07 | | 0.04 | 99.85 | 0.02 | |

EXAMPLE 18

Preparation of Micronized (5+5) Bis Bortezomib L-Tartrate III 40 mg (5+5) bis bortezomib L-tartrate III prepared as described in example 2 were micronized in a suitable equipment.

The micronized product was analyzed by using mastersizer Microplus (Malvern) through LALLS technique using silicone oil as dispersing medium.

The results expressed as particle size of the powder are reported in the following table.

| | | |
| --- | --- | --- |
| Residual = 0.683% | Concentration = 0.009% | Obscuration = 26.34% |
| d(0.5) = 2.09 μm | d(0.1) = 1.06 μm | d(0.9) = 3.95 μm |
| D[4, 3] = 2.33 μm | Span = 1.38 | d(0.95) = 4.62 μm |
| Sauter mean | | Mode = 2.34 |
| D[3, 2] = 1.83 μm | | |

The product was analyzed with the method reported in example 9, obtaining the following HPLC purity data.

|  | Retention time (min) | | | | | |
| --- | --- | --- | --- | --- | --- | --- |
|  | 23.58 | 24.57 | 25.78 | 27.00 | 28.00 | 28.77 |
|  | | | Relative retention time | | | |
| Sample | 0.87 | 0.91 | 0.95 | 1.00 | 1.037 | 1.07 |
| t0 | 0.03% | | | 99.72% | 0.06% | 0.03% |

EXAMPLE 19

Solubility Test of Solid Mixture of Micronized (5+5) Bis Bortezomib L-Tartrate III with Inorganic Salts A micronized product prepared as described in example 18 was mixed with $NaH_2PO_4$/$Na_2HPO_4$ and with disodium tartrate.

In the following table the solubility results of said solid mixtures are reported.

| Micronized sample (mg) | Excipient | Bortezomib:excipient ratio | Homogenization method | Diluent (5 ml) | Solubility |
| --- | --- | --- | --- | --- | --- |
| 5 | $NaH_2PO_4$/$Na_2HPO_4$ 1:1 micronized | 1:10 | Powders separately weighed in vial | NaCl 0.9% | >300 sec |
| 5 | Micronized disodium tartrate | 1:10 | With pestle and mortar | NaCl 0.9% | 120 sec |
| 5 | Micronized disodium tartrate | 1:10 | With pestle and mortar | NaCl 0.9% + phosphate buffer pH = 7.3 | 120 sec |

EXAMPLE 20

Stability Tests of (5+5) Bis Bortezomib Tartrate III in DMSO Solution with Acid Stabilizers Preparation of sample A:

In a 10 ml flask 400 mg (5+5) Bis-bortezomib tartrate III, prepared as described in example 2, and 10 mg L-tartaric acid were weighed. The mixture was dissolved and brought to volume with DMSO (pharmaceutical grade).

Preparation sample B:

In a 10 ml flask 400 mg (5+5) Bis-bortezomib tartrate III, prepared as described in example 2, and 7 μl 85% phosphoric acid acid were weighed. The mixture was dissolved and brought to volume with DMSO (pharmaceutical grade).

In the following table the data of the HPLC purity analysis of the solution at time 0 and after 1 month, 2 months and 3 months of storage in glass vials with screw cap and hermetic closure at 40° C. are reported.

|   |   | Retention time (min) | | | | | |
|---|---|---|---|---|---|---|---|
|   |   | 23.58 | 24.57 | 25.78 | 27.00 | 28.00 | 28.77 |
|   |   | | | Relative retention time | | | |
|   | Sample | 0.87 | 0.91 | 0.95 | 1.00 | 1.037 | 1.07 |
| A | t0 | | | | 99.99 | 0.01 | |
|   | 1 month 40° C. | 0.03 | | | 99.84 | | |
|   | 2 months 40° C. | 0.03 | | 0.02 | 99.85 | | 0.01 |
|   | 3 months 40° C. | 0.03 | | | 99.95 | | 0.02 |
| B | t0 | | | | 99.99 | 0.01 | |
|   | 1 month 40° C. | | | | 99.95 | 0.02 | 0.03 |
|   | 2 months 40° C. | 0.02 | | 0.02 | 99.86 | 0.01 | |
|   | 3 months 40° C. | 0.13 | | | 99.74 | 0.02 | 0.06 |

The invention claimed is:

1. An ester of bortezomib with tartaric acid wherein bortezomib and tartaric acid are in molar ratio 2:1.

2. An ester of bortezomib according to claim 1 of formula

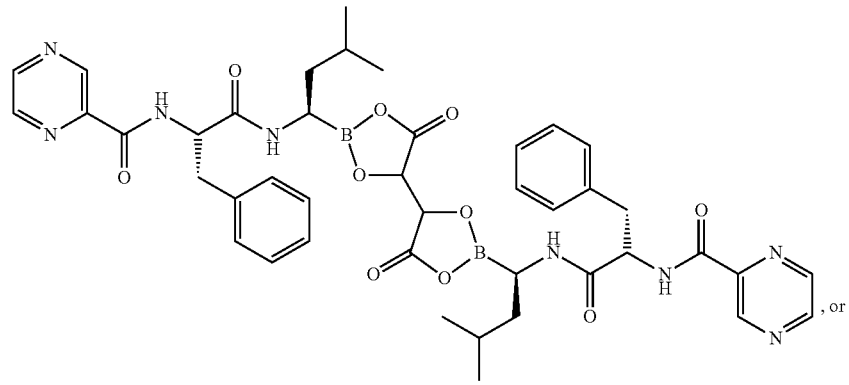

(III)

, or

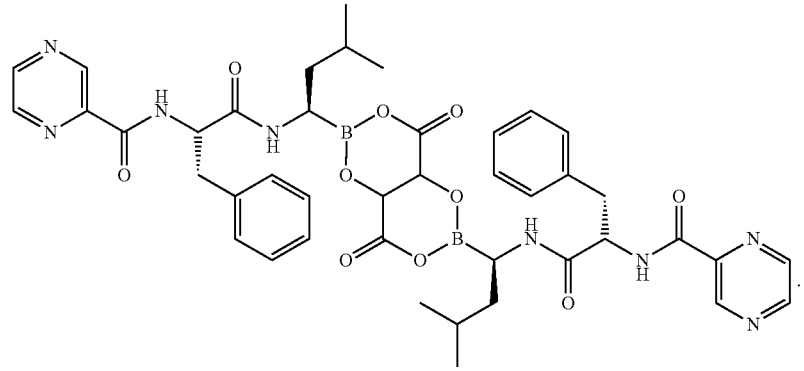

(IV)

.

3. Crystalline and amorphous forms of an ester according to claim 1.

4. An ester according to claim 1, wherein tartaric acid is L-tartaric acid.

5. A formulation containing an ester of bortezomib according to claim 1 in admixture with pharmaceutically acceptable excipients.

6. The formulation according to claim 5 in liquid form.

7. Injectable solutions obtained by reconstitution of a formulation according to claim 5 with physiologically compatible solutions.

* * * * *